(12) United States Patent
Iwakami et al.

(10) Patent No.: US 10,301,636 B2
(45) Date of Patent: May 28, 2019

(54) PLANT CELL COMPRISING MUTATION INTRODUCED IN TARGET DNA, AND METHOD FOR PRODUCING THE PLANT CELL

(71) Applicant: NATIONAL RESEARCH AND DEVELOPMENT AGENCY NATIONAL AGRICULTURE AND FOOD RESEARCH ORGANIZATION, Tsukuba-shi, Ibaraki (JP)

(72) Inventors: Masaki Iwakami, Tsukuba (JP); Seiichi Toki, Tsukuba (JP)

(73) Assignee: NATIONAL RESEARCH AND DEVELOPMENT AGENCY NATIONAL AGRICULTURE AND FOOD RESEARCH ORGANIZATION, Tsukuba-shi, Ibaraki (JP)

( * ) Notice: Subject to any disclaimer, the term of this patent is extended or adjusted under 35 U.S.C. 154(b) by 0 days.

(21) Appl. No.: 15/121,458

(22) PCT Filed: Feb. 24, 2015

(86) PCT No.: PCT/JP2015/055230
§ 371 (c)(1),
(2) Date: Aug. 25, 2016

(87) PCT Pub. No.: WO2015/129686
PCT Pub. Date: Sep. 3, 2015

(65) Prior Publication Data
US 2016/0362699 A1    Dec. 15, 2016

(30) Foreign Application Priority Data

Feb. 25, 2014  (JP) ................................. 2014-034009

(51) Int. Cl.
*C12N 15/82*     (2006.01)
(52) U.S. Cl.
CPC .............................. *C12N 15/8213* (2013.01)
(58) Field of Classification Search
None
See application file for complete search history.

(56) References Cited

U.S. PATENT DOCUMENTS

2013/0024998 A1*  1/2013  Paul ...................... C12N 15/82
                                                                   800/276

FOREIGN PATENT DOCUMENTS

| JP | 2005-519631 A | 7/2005 |
| JP | 2013-514764 A | 5/2013 |
| JP | 2013-529915 A | 7/2013 |
| WO | 03/087341 A2 | 10/2003 |
| WO | 2011/078665 A1 | 6/2011 |
| WO | 2011/154393 A1 | 12/2011 |

OTHER PUBLICATIONS

Fauser et al. In planta gene targeting. (2012) PNAS; vol. 109; pp. 7535-7540.*
Rubnitz et al. The minimum amount of homology required for homologous recombination in mammalian cells. (1984) Molecular and Cellular Biology; vol. 4; pp. 2253-2258 (Year: 1984).*
Rie Terada et al. "Cre-IoxP mediated marker elimination and gene reactivation at the waxy locus created in rice genome based on strong positive-negative selection", Plant Biotechnology, 2010, pp. 29-37, vol. 27.
Yong-Ik Kwon et al., "Overexpression of OsRecQI4 and/or OsExo1 Enhances DSB-Induced Homologous Recombination in Rice", Plant Cell Physiology, 2012, pp. 2142-2152, vol. 53, No. 12.
Ayako Yokoi et al., "The development of targeted genome engineering in plants", Regulation of Plant Growth & Development, Dec. 20, 2013, pp. 117-124, vol. 48, No. 2.
Masaki Endo et al., "Shokubutsu Genome no Hyoteki Idenshi Kaihen ni Okeru Jinko Seigen Koso no Riyo", Biotechnology, Aug. 25, 2013, pp. 348-351, vol. 91, No. 8.
Ayako Yokoi et al., "Ine no Hyoteki Idenshi Kaihen Gijutsu no Tenkai", Dai 31 Kai Japanese Society for Plant Cell and Molecular Biology (Sapporo) Taikai Symposium Koen Yoshishu, Aug. 20, 2013, 3 pages.
International Search Report for PCT/JP2015/055230 dated Jun. 2, 2015.
International Preliminary Report on Patentability issued from the International Bureau in counterpart International Application No. PCT/JP2015/055230, dated Sep. 9, 2016.
Endo, Masaki et al., "Toward establishing an efficient and versatile gene targeting system in higher plants", Biocatalysis and Agricultural Biotechnology, Oct. 11, 2013, vol. 3, pp. 2-6.
Iida et al., "Modification of endogenous natural genes by gene targeting in rice and other higher plants", Plant Molecular Biology, 2005 vol. 59, pp. 205-219.
Communication, dated Sep. 27, 2018, issued by the Japanese Patent Office in Japanese Application No. 2015-033825.

(Continued)

*Primary Examiner* — Cathy Kingdon Worley
(74) *Attorney, Agent, or Firm* — Sughrue Mion, PLLC

(57) ABSTRACT

It has been found that a marker gene, which is inserted in the genomic DNA via homologous recombination, and to both ends of which nuclease recognition sites are added, can be removed from a plant cell by using a corresponding nuclease, and further that the nuclease recognition sites can also be removed without leaving any trace by matching sequences of at least 30 nucleotides adjacent to the recognition sites. Moreover, in a method for introducing a mutation into a target DNA on the genome of a plant cell via homologous recombination, it is made possible to: stably select a plant cell, in which the mutation is introduced, based on an expression of a marker gene; further, to remove an unnecessary sequence such as the marker gene from the selected cell; and to introduce only a required mutation into the target DNA.

12 Claims, 14 Drawing Sheets

Specification includes a Sequence Listing.

(56) References Cited

OTHER PUBLICATIONS

Dang et al., "Gene Editing a Constitutively Active OsRac1 by Homologous Recombination-Based Gene Targeting Induces Immune Responses in Rice," Plant Cell Physiology, 2013, 54(12): 2058-2070.

Puchta et al., "Towards the ideal GMP: Homologous recombination and marker gene excision," J. Plant Physiol., 2003, vol. 160, p. 743-754.

* cited by examiner

PLANT CELL COMPRISING MUTATION INTRODUCED IN TARGET DNA, AND METHOD FOR PRODUCING THE PLANT CELL

CROSS REFERENCE TO RELATED APPLICATIONS

This application is a National Stage of International Application No. PCT/JP2015/055230filed Feb. 24, 2015, claiming priority based on Japanese Patent Application No. 2014-034009 filed Feb. 25, 2014, the contents of all of which are incorporated herein by reference in their entirety.

TECHNICAL FIELD

The present invention relates to a plant cell comprising a mutation introduced in a target DNA, and a plant comprising the plant cell, as well as a progeny, a clone, and a propagation material of the plant. Moreover, the present invention relates to a method for producing the plant cell, a DNA construct for use in the production method, and a kit comprising the DNA construct.

BACKGROUND ART

Gene targeting (GT) is a technique of modifying a target DNA on a genome at will by recombination utilizing the base sequence homology of DNAs. In the field of plants also, this technique is very promising in the fundamental research and in the development of breeding materials.

Nevertheless, the frequency of the homologous recombination in higher plants is low. When vector shaving a certain mutation on a sequence homologous to a target DNA (GT vectors) are introduced into cells from the outside to modify the target DNA via GT, most of the vectors are randomly inserted into the genomes. Against this background, positive-negative selection has been developed to efficiently select cells in which GT has successfully occurred. This method is a selection method in which cells having GT vectors randomly incorporated in the genomes are eliminated on the basis of the expression of a negative selectable marker gene, while cells having mutations introduced in target DNAs by GT are isolated on the basis of the expression of a positive selectable marker gene (NPL 1).

However, when this method is used, the expression cassette of the positive selectable marker gene remains in the target DNA. Accordingly, this cassette needs to be removed in a case where only a required mutation is to be introduced into a target DNA. In this regard, there has been a report so far on a system in which a positive selectable marker gene is removed after GT using a site-specific recombinase. Nevertheless, when this system is used, the recognition sequence of the site-specific recombinase remains after the marker is removed. Since it is also reported that even inserting a short base sequence influences the expressions of adjacent genes, there has been a demand for the development of a technique capable of marker removal without leaving any footprint after GT, and used when an introduction system is constructed for a mutation equivalent to a spontaneous mutation.

In relation to the technique of removing a marker gene, the present inventors have revealed the following findings. To be more specific, first, a T-DNA having a reporter gene in which a marker gene and recognition sites of a nuclease I-SceI disposed on both ends of the marker gene are inserted is introduced into plant cells. Then, the marker gene can be removed from the reporter gene by expressing I-SceI in a plant cell in which the reporter gene is randomly inserted in the genomic DNA. In this approach, as in the case of utilizing the above-described site-specific recombinase, if the two I-SceI recognition sites are simply utilized to excise the selectable marker gene, broken ends are rejoined, leaving the I-SceI recognition sites in the genomic DNA. For this reason, the present inventors have further devised a scheme of matching (overlapping) 600-bp sequences located outside the recognition sites in the T-DNA. Thereby, after the marker gene is excised, homologous recombination occurs between the overlapping DNA sequences of broken ends, and the I-SceI recognition sites are also successfully removed (NPL 2).

However, in the method described in NPL 2, homologous recombination occurs between the overlapping DNA sequences before I-SceI is expressed. As a result, the marker gene is removed in quite a large amount from the genomic DNAs. This brings about a problem that it is difficult to select a plant cell, in which a reporter gene is randomly inserted in the genomic DNA, based on an expression of the marker gene.

Hence, for the application to GT of such a marker gene removal technique via homologous recombination between overlapping DNA sequences, it has been required to further develop a technique for stably selecting a cell, in which a mutation is introduced in a target DNA, based on an expression of a marker gene.

CITATION LIST

Non Patent Literatures

[NPL 1] Terada R. et al., Plant Biotechnol., 2010, Vol. 27, pp. 29 to 37

[NPL 2] Yong-Ik Kwon et al., Plant Cell Physiol., 2012, Vol. 53, No. 12, pp. 2142 to 2152

SUMMARY OF INVENTION

Technical Problem

The present invention has been made in view of the problems of the above-described conventional techniques. An object of the present invention is to enable, in a method for introducing a mutation into a target DNA on the genome of a plant cell via homologous recombination: stable selection of a plant cell, in which the mutation is introduced, based on an expression of a marker gene; further, removal of an unnecessary sequence such as the marker gene from the selected cell; and introduction of only a required mutation into the target DNA.

Solution to Problem

The present inventors have earnestly studied in order to achieve the above object. As a result, the inventors have come up with an idea of a system shown in FIG. 1 for enabling an introduction of only a required mutation into a target DNA in a plant cell without leaving any unnecessary sequence such as a marker gene.

To be more specific, first, as shown in a first step in FIG. 1, homologous recombination is allowed to occur by introducing into plant cells a DNA construct comprising: a marker gene; and a first DNA and a second DNA homologous to a target DNA.

Note that, in this DNA construct,
(a) the first homologous DNA is added to a 5' side of the marker gene via a first nuclease recognition site,
(b) the second homologous DNA is added to a 3' side of the marker gene via a second nuclease recognition site,
(c) a 3' end region of the first homologous DNA and a 5' end region of the second homologous DNA are DNA sequences having 30 to 500 nucleotides (short overlapping DNA sequences) homologous to each other, and
(d) in at least one DNA of the first homologous DNA and the second homologous DNA, a desired mutation is introduced in a region other than the short overlapping DNA sequence.

As a result of the homologous recombination between the target DNA on the genomic DNA of a plant cell and the first and second homologous DNAs, the mutation and the marker gene flanked by the first and second nuclease recognition sites are introduced in the target DNA.

Then, the plant cell, in which the mutation and so forth are introduced in the target DNA, is selected by screening based on an expression of the marker gene.

Further, as shown in a second step in FIG. 1, a nuclease capable of specifically recognizing the first and second nuclease recognition sites is expressed in the cell selected as described above. The nuclease cleaves the first and second nuclease recognition sites, and the marker gene is removed from the target DNA. Further, homologous recombination occurs between the short overlapping DNA sequences adjacent to the first and second nuclease recognition sites thus cleaved, and these nuclease recognition sites are also removed.

Thus, according to this idea, it is possible to prepare a mutant plant having only a desired mutation in a target DNA.

Hence, the system shown in FIG. 1 was actually constructed to verify the effectiveness. The result has revealed for the first time that the marker gene inserted in the genomic DNA via homologous recombination can be removed from the plant cell by using the nuclease, and further that the nuclease recognition sites can also be removed without leaving any trace by matching (overlapping) the 30-nucleotide sequences adjacent to the recognition sites. In addition, by restricting the length of the short overlapping DNA sequence to 30 nucleotides, homologous recombination is less likely to occur between the short overlapping DNA sequences before the nuclease is expressed, than NPL 2. This enables stable selection of a plant cell, in which the mutation and so forth are introduced, based on the expression of the marker gene.

It should be noted that the correlation of the number of nucleotides in short overlapping DNA sequences with the frequency of homologous recombination between the short overlapping DNA sequences in the absence of nuclease expression was evaluated using systems shown in FIG. 13. As a result, when the length of the short overlapping DNA sequences was 1000 nucleotides, homologous recombination occurred in cells even before the nuclease was expressed; the homologous recombination occurred in approximately 30 percent of cell masses (calli) used in the analysis. On the other hand, when the length of the short overlapping DNA sequences was 30 nucleotides, the occurrence of the homologous recombination in the absence of nuclease expression was completely suppressed.

Thus, the present invention relates to: a method for producing a plant cell comprising only a required mutation introduced in a target DNA without leaving any unnecessary sequence such as a marker gene not only in the target DNA but also in regions other than the DNA; a plant cell produced by the method; and a kit and so forth for use in the production method. More specifically, the present invention provides the following inventions.

(1) A method for producing a plant cell comprising a mutation introduced in a target DNA, the method comprising the following steps (i) to (iii):
(i) a step of introducing into plant cells a DNA construct comprising a marker gene, and a first DNA and a second DNA homologous to a target DNA, the DNA construct having the following features (a) to (d)
(a) the first homologous DNA is added to a 5' side of the marker gene via a first nuclease recognition site,
(b) the second homologous DNA is added to a 3' side of the marker gene via a second nuclease recognition site,
(c) a 3' end region of the first homologous DNA and a 5' end region of the second homologous DNA are DNA sequences having 30 to 500 nucleotides (short overlapping DNA sequences) homologous to each other, and
(d) in at least one DNA of the first homologous DNA and the second homologous DNA, a desired mutation is introduced in a region other than the short overlapping DNA sequence;
(ii) a step of selecting a plant cell, in which the mutation and the marker gene flanked by the first and second nuclease recognition sites are introduced in the target DNA via homologous recombination between the target DNA and the first and second homologous DNAs, based on an expression of the marker gene; and
(iii) a step of removing the marker gene and the first and second nuclease recognition sites from the target DNA by expressing a nuclease capable of specifically recognizing the first and second nuclease recognition sites in the cell selected in the step (ii).

(2) The method according to (1), wherein the nuclease is I-SceI.

(3) A plant cell comprising a mutation introduced in a target DNA, and produced by the method according to (1) or (2).

(4) A plant cell comprising a marker gene flanked by first and second nuclease recognition sites, and the following mutation introduced in a target DNA via homologous recombination with a first DNA and a second DNA homologous to the target DNA by introducing a DNA construct comprising the marker gene and the first and second homologous DNAs, the DNA construct having the following features (a) to (d):
(a) the first homologous DNA is added to a 5' side of the marker gene via a first nuclease recognition site;
(b) the second homologous DNA is added to a 3' side of the marker gene via a second nuclease recognition site;
(c) a 3' end region of the first homologous DNA and a 5' end region of the second homologous DNA are DNA sequences having 30 to 500 nucleotides (short overlapping DNA sequences) homologous to each other; and
(d) in at least one DNA of the first homologous DNA and the second homologous DNA, a desired mutation is introduced in a region other than the short overlapping DNA sequence.

(5) The plant cell according to (4), wherein the nuclease is I-SceI.

(6) A plant comprising the cell according to any one of (3) to (5).

(7) A plant which is any one of a progeny and a clone of the plant according to (6).

(8) A propagation material of the plant according to (6) or (7).

(9) A DNA construct comprising: a marker gene; and a first DNA and a second DNA homologous to a target DNA, the DNA construct having the following features (a) to (d):
  (a) the first homologous DNA is added to a 5' side of the marker gene via a first nuclease recognition site;
  (b) the second homologous DNA is added to a 3' side of the marker gene via a second nuclease recognition site;
  (c) a 3' end region of the first homologous DNA and a 5' end region of the second homologous DNA are DNA sequences having 30 to 500 nucleotides (short overlapping DNA sequences) homologous to each other; and
  (d) in at least one DNA of the first homologous DNA and the second homologous DNA, a desired mutation is introduced in a region other than the short overlapping DNA sequence.
(10) A kit for use in the method according to (1) or (2), the kit comprising the following (a) and (b):
  (a) the DNA construct according to (9); and
  (b) a DNA construct for expressing in a plant cell a nuclease capable of specifically recognizing the first and second nuclease recognition sites.

Advantageous Effects of Invention

In a method for introducing a mutation into a target DNA on the genome of a plant cell via homologous recombination, the present invention makes it possible to stably select a plant cell, in which the mutation is introduced, based on an expression of a marker gene. Further, the present invention also makes it possible to remove an unnecessary sequence such as the marker gene in the selected cell, and to introduce only a required mutation into the target DNA.

DESCRIPTION OF EMBODIMENTS

Figure 1:
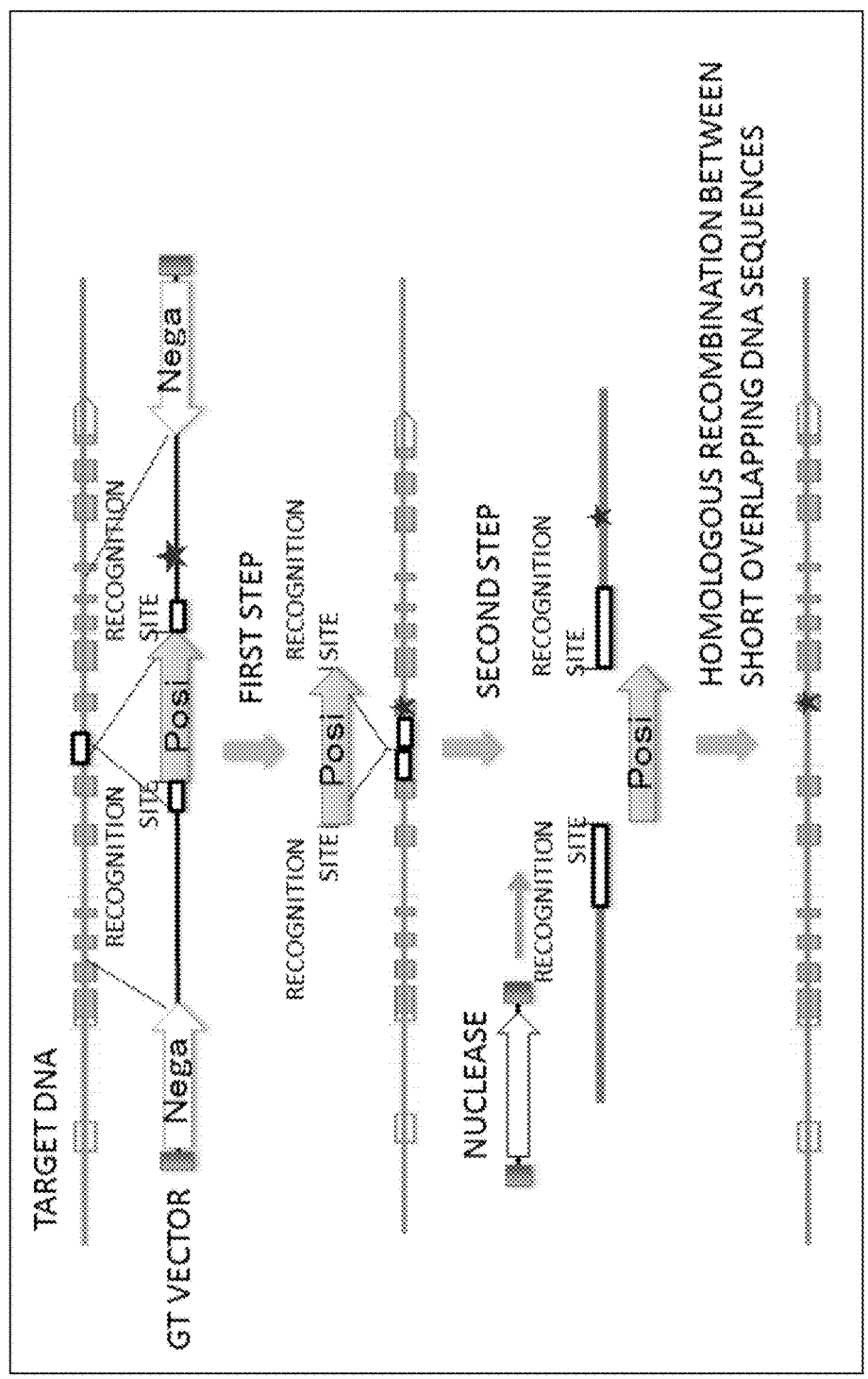
FIG. 1 is a schematic diagram for illustrating a method for producing a plant cell comprising a mutation introduced in a target DNA of the present invention. In the figure, an arrow denoted by "Posi" on a GT vector represents a marker gene (positive select able marker gene), and a pair of arrows denoted by "Nega" on the GT vector represent negative selectable marker genes. A star indicates a desired mutation site to be introduced into the target DNA. An arrow denoted by nuclease represents a DNA encoding the nuclease, and each "recognition site" indicates a site which the nuclease specifically recognizes and cleaves. Moreover, each white square, which is added to the arrow denoted by Posi via a recognition site, represents a short overlapping DNA sequence. Further, black bars provided on both sides of the arrow denoted by nuclease and on both sides of the pair of arrows on the GT vector represent right boundary sequences (RB) and left boundary sequences (LB) utilized when DNAs encoding the GT vector and the nuclease are introduced into a plant cell using *Agrobacterium*. Note that, regarding the representations in the figure, the same shall apply also to FIGS. 2, 3, 5, and 9.

A method for producing a plant cell of the present invention is a method for producing a plant cell comprising a mutation introduced in a target DNA, the method comprising the following steps (i) to (iii):

(i) a step of introducing into plant cells a DNA construct comprising a marker gene, and a first DNA and a second DNA homologous to a target DNA, the DNA construct having the following features (a) to (d)

(a) the first homologous DNA is added to a 5' side of the marker gene via a first nuclease recognition site, (b) the second homologous DNA is added to a 3' side of the marker gene via a second nuclease recognition site, (c) a 3' end region of the first homologous DNA and a 5' end region of the second homologous DNA are DNA sequences having 30 to 500 nucleotides (short overlapping DNA sequences) homologous to each other, and (d) in at least one DNA of the first homologous DNA and the second homologous DNA, a desired mutation is introduced in a region other than the short overlapping DNA sequence;

(ii) a step of selecting a plant cell, in which the mutation and the marker gene flanked by the first and second nuclease recognition sites are introduced in the target DNA via homologous recombination between the target DNA and the first and second homologous DNAs, based on an expression of the marker gene; and (iii) a step of removing the marker gene and the first and second nuclease recognition sites from the target DNA by expressing a nuclease capable of specifically recognizing the first and second nuclease recognition sites in the cell selected in the step (ii).

According to the method, homologous recombination occurs between the DNA construct and a target DNA on the genomic DNA of a plant cell as described later in Examples, thereby introducing a desired mutation and the marker gene flanked by the first and second nuclease recognition sites into the target DNA. Then, a plant cell, in which the mutation and so forth are introduced in the target DNA, can be selected by screening based on an expression of the marker gene. Further, by expressing the nuclease capable of specifically recognizing the first and second nuclease recognition sites, the nuclease cleaves the first and second nuclease recognition sites, and the marker gene can be removed from the target DNA. Subsequently, homologous recombination occurs between the short overlapping DNA sequences adjacent to the first and second nuclease recognition sites thus cleaved, and these nuclease recognition sites can also be removed. Thus, in a method for introducing a mutation into a target DNA on the genome of a plant cell via homologous recombination, the present invention makes it possible to stably select a plant cell, in which the mutation is introduced, based on an expression of a marker gene. Further, the present invention also makes it possible to remove an unnecessary sequence such as the marker gene in the selected cell, and to introduce only a required mutation into the target DNA (see FIG. 1).

The "DNA construct" to be introduced into a plant cell in order to introduce a mutation to a target DNA in the step (i) of the production method of the present invention is a DNA construct comprising a marker gene, and a first DNA and a second DNA homologous to a target DNA, the DNA construct having the above-described features (a) to (d).

In the present invention, the term "target DNA" means a DNA on a genome to which a mutation is to be introduced. Any target DNA can be selected from the genomic DNA of a plant cell, and may be a DNA encoding a protein, or may be a DNA encoding a non-coding RNA such as a functional RNA. Further, the target DNA includes not only regions (such as UTR) encoding no protein or non-coding RNA, but also regions regulating expressions of non-coding RNAs and transcription products encoding proteins. Additionally, the target DNA is normally an endogenous DNA, but may be a DNA exogenously inserted into the genomic DNA of a plant cell.

The "mutation" to be introduced into the target DNA is not particularly limited, and may be a silent mutation or may be a null mutation such as a nonsense mutation, a frameshift mutation, an insertion mutation, or a splice site mutation. Moreover, examples of the mutation in the target DNA include deletion, substitution, addition, and/or insertion of one or more nucleotides in the DNA. Further, the number of mutations in the target DNA is not particularly limited, and may be one or more than one.

The term "DNA homologous to a target DNA" means a DNA having a homology with the above-described target DNA on the genome. In the DNA construct of the present invention, the "DNA homologous to a target DNA" includes: a first homologous DNA added to a 5' side of a marker gene to be described later via a first nuclease recognition site to be described later; and a second homologous DNA added to a 3' side of the marker gene to be described later via a second nuclease recognition site to be described later.

The number of nucleotides in each of the first homologous DNA and the second homologous DNA should be such a number that homologous recombination can occur between the homologous DNA and the target DNA. Normally, the first homologous DNA and the second homologous DNA each have 500 to 7000 nucleotides (preferably 1000 to 5000 nucleotides, more preferably 2000 to 4000 nucleotides, and furthermore preferably approximately 3000 nucleotides (for example, 2500 to 3000)).

Moreover, in the present invention, it is necessary that a 3' end region of the first homologous DNA and a 5' end region of the second homologous DNA be DNA sequences having 30 to 500 nucleotides (in the present invention, also referred to as "short overlapping DNA sequences") homologous to each other, preferably DNA sequences having 30 to 300 nucleotides homologous to each other, and more preferably DNA sequences having 30 to 100 nucleotides homologous to each other. If the number of nucleotides in the short overlapping DNA sequences is less than the lower limit, homologous recombination is unlikely to occur between the short overlapping DNA sequences after the nuclease recognition sites are cleaved by the nuclease capable of specifically recognizing the first and second nuclease recognition sites. In this event, there is a trend that the first and second nuclease recognition sites are likely to remain in the target DNA. On the other hand, if the number of nucleotides in the short overlapping DNA sequences exceeds the upper limit, homologous recombination occurs between the short overlapping DNA sequences before the nuclease recognition sites are cleaved by the nuclease capable of specifically recognizing the first and second nuclease recognition sites. In this event, the nuclease recognition sites and the marker gene flanked by these recognition sites are likely to be removed from the target DNA. For this reason, in the step (ii), it tends to be hard to select a plant cell, in which a desired mutation and so forth are introduced in the target DNA, based on the expression of the marker gene.

Further, it is necessary that, in at least one DNA of the first homologous DNA and the second homologous DNA, the mutation be introduced in a region other than the short overlapping DNA sequence. This is to prevent the mutation introduced in the target DNA from being removed via the homologous recombination between the short overlapping DNA sequences, and to leave the mutation in the target DNA.

The first and second nucleotide recognition sequences added between the marker gene to be described later and the first and second homologous DNAs, respectively should be sequences specifically recognized and cleaved by the nuclease to be described later. Moreover, the first and second nucleotide recognition sequences may be sequences specifically recognized by the same nuclease, or may be sequences specifically recognized by different nucleases, respectively. Nevertheless, it is preferable that one type of the nuclease to be expressed in the step (ii) described later be prepared, and that the sequences be specifically recognized by the same nuclease, from the viewpoint of reducing the labors for transformation and so forth. Further, in a case where the first and second nucleotide recognition sequences are sequences specifically recognized by the same nuclease and are asymmetrical sequences, the direction of the first nucleotide recognition sequence is preferably opposite to that of the second nucleotide recognition sequence. This is because if the direction of the first nucleotide recognition sequence is the same as that of the second nucleotide recognition sequence, when the sequences are cleaved by the nuclease, end sequences resulting from the cleavage are likely to rejoin, so that the homologous recombination between the short overlapping DNA sequences is unlikely to occur.

The expression of the "marker gene" flanked by the first and second nuclease recognition sites should serve as an indicator for efficiently selecting a small number of transformed cells comprising the target DNA out of a large number of non-transformed cells. Examples thereof include genes encoding proteins essential for the growth of the modified cells or proteins for promoting the growth (in other words, positive selectable marker genes such as chemical resistance genes), and reporter genes such as a luciferase gene, a GFP gene, a CFP gene, a YFP gene, and a DsRed gene. From the viewpoint of requiring no complicated operation (for example, FACS screening) for detecting the marker gene expression, chemical resistance genes are preferable. Examples of the chemical resistance genes include a neomycin (such as G418) resistance gene (NPTII gene), a hygromycin resistance gene (hygromycin phosphotransferase gene, hpt), and a kanamycin resistance gene; and herbicide resistance genes such as an ALS (AHAS) gene and a PPO gene.

Moreover, in the DNA construct of the present invention, a regulatory region for expressing a protein encoded by the marker gene introduced in the plant cell is operably linked to the gene.

For constitutively expressing the protein, examples of the regulatory region include promoters such as a cauliflower mosaic virus (CaMV) 35S promoter, a G10-90 promoter, a nopaline synthase gene promoter, acorn-derived polyubiquitin-1 promoter, a rice-derived actin promoter, and a rice-derived elongation factor 1α promoter; and terminator sequences for terminating the transcription of genes induced by the promoters or the like (such as a pea-derived rubisco E9 gene terminator (Tpea rbs E9), a pea-derived rubisco 3A gene terminator (Tpea 3A), a rice-derived heat shock protein 17.3 terminator, a rice-derived heat shock protein 16.9a terminator, a rice-derived actin terminator, a nopaline synthase gene terminator, an octopine synthase (OCS) gene terminator, and a CaMV 35S terminator). Further, the regulatory region may contain an enhancer to increase the gene expression efficiency, such as a CaMV 35S enhancer, a transcription enhancer E12, or enhancers of an omega sequence or the like.

Moreover, for inducible expression of the protein, it is suitable to use a promoter which induces the expression in response to a stimulus, for example, a rice chitinase gene promoter, a tobacco PR protein gene promoter, a rice lip19 gene promoter, rice hsp80 gene and hsp72 gene promoters, an Arabidopsis thaliana rab16 gene promoter, a parsley chalcone synthase gene promoter, a corn alcohol dehydrogenase gene promoter, a promoter which induces the expression in response to a chemical such as estradiol (β-estradiol), tetracycline, or dexamethasone, or other similar promoters.

Meanwhile, in addition to the marker gene, another DNA(s) may be inserted in the DNA construct of the present invention, as long as the other DNAs are disposed between the first and second nucleotide recognition sequences. The other DNAs are not particularly limited. Nevertheless, an example thereof includes a terminator for inactivating a protein or the like encoded by the target DNA in which the marker gene and so forth are inserted. Moreover, in order to omit a step of introducing a DNA construct again for expressing a nuclease to remove the marker gene and so forth from the target DNA after the above-described DNA construct is introduced, the example includes a DNA construct (expression cassette) capable of inducibly expressing the nuclease.

In the "DNA construct" of the present invention, a gene encoding a protein for inhibiting the growth of the modified cells or a protein for suppressing the growth (in other words, negative selectable marker gene) may be added to each of a 5' end of the first homologous DNA and a 3' end of the second homologous DNA (see the "GT vector" in FIG. 1).

Examples of the "negative selectable marker gene" include a diphtheria toxin a subunit (DT-A) gene, a codA gene, an exotoxin A gene, a ricin toxin A gene, a cytochrome P-450 gene, an RNase T1 gene, and a barnase gene. Among these, a DT-A gene is preferable for rice calli and the like from the viewpoints of the negative selection efficiency and not affecting the surrounding cells because of the lack of the intracellular movement ability. Moreover, as in the case of the above-described marker gene, a regulatory region for expressing a protein encoded by the negative selectable marker gene introduced in the plant cell is operably linked to the gene in the DNA construct of the present invention.

Further, when the DNA construct containing such a negative selectable marker gene is introduced into a plant cell, the negative selectable marker gene is never inserted into the genomic DNA of the cell as a result of incorporating a portion (the DNA homologous to the target DNA) of the DNA construct into the target DNA via homologous recombination. This is because the negative selectable marker gene is located outside the homologous DNA. Hence, the plant cell can grow without the influence from the gene. On the other hand, if the DNA construct is randomly inserted into the genomic DNA of a plant cell, the negative selectable marker gene may also be inserted therein, so that the growth of the plant cell having such a random insertion may be suppressed or inhibited. Thus, introducing the DNA construct containing the negative selectable marker gene into a plant cell does not cause a random insertion, making it possible to efficiently select the plant cell comprising the mutation introduced in the target DNA via homologous recombination.

Although the "DNA construct" of the present invention has been described above, the method for introducing such a DNA construct into plant cells in the step (i) of the production method of the present invention is not particularly limited. It is possible to use various methods known to those skilled in the art such as an *Agrobacterium*-mediated method, a polyethylene glycol method, an electroporation method (electroporation), and a particle gun method.

Next, in the step (ii) of the production method of the present invention, a plant cell, in which the mutation and the marker gene flanked by the first and second nuclease recognition sites are introduced in the target DNA via homologous recombination between the target DNA and the first and second homologous DNAs, is selected based on an expression of the marker gene.

Those skilled in the art can perform such a "selection" by selecting a known approach as appropriate in accordance with the type of the marker gene to be used. For example, in the case of using a chemical resistance gene, if the plant cell having the DNA construct of the present invention introduced in the step (i) is cultured in the presence of a corresponding chemical, a plant cell, in which the mutation and so forth are introduced in the target DNA, can be selected. In the case of using a reporter gene such as a GFP gene, if the plant cell having the DNA construct of the present invention introduced in the step (i) is subjected to FACS or the like, a plant cell, in which the mutation and so forth are introduced in the target DNA, can be selected.

Additionally, besides the selection based on the expression of the marker gene, the step may comprise confirming the introduction of the mutation, the marker gene, and so forth into the target DNA via the homologous recombination, by a PCR method, a sequencing method, a Southern blotting method, a CAPS (cleaved amplified polymorphic sequence) method, or the like.

Next, the marker gene and the first and second nuclease recognition sites are removed from the target DNA by expressing the nuclease capable of specifically recognizing the first and second nuclease recognition sites in the cell selected in the step (ii).

In the present invention, the "nuclease" should be an enzyme capable of recognizing a specific sequence and cleaving a site within the sequence. Examples thereof include homing endonuclease such as I-SceI and I-CreI, and artificial nucleases such as ZFN (zinc finger nuclease), TALEN, and CRISPR/Cas9. I-SceI is preferable from the viewpoints that: the cleavage activity is high, the recognition sequence does not exist in the genomic DNA of rice and the like, and the mutation is unlikely to be introduced into a region other than the target DNA.

Note that those skilled in the art can prepare DNAs encoding these nucleases as appropriate with reference to the description of Belfort M. et al., Nucleic Acids Res, 1997, Vol. 25, Iss. 17, pp. 3379 to 3388 in the case of homing endonucleases such as I-CreI; particularly in the case of I-SceI, with reference also to the descriptions of Puchta H. et al., Nucleic Acids Res., 1993, Vol. 21, Iss. 22, pp. 5034 to 5040, Salomon & Puchta, EMBO J., 1998, Vol. 17, Iss. 20, pp. 6086 to 6095, and so on; in the case of ZFN, with reference to the descriptions of Japanese Patent Nos. 4350907 and 4555292, and so on; in the case of TALEN, with reference to the descriptions of International Application Japanese-Phase Publication Nos. 2012-514976 and 2013-513389, and so on; in the case of CRISPR/Cas9, with reference to the descriptions of Jinek et al., Science, 2012, Vol. 337, pp. 816 to 821, Mali et al., Science, 2013, Vol. 339, pp. 823 to 826, and so on. Further, the first and second nuclease recognition sequences can also be prepared based on the descriptions of these literatures.

Moreover, a functional protein may be added to the "nuclease" in the present invention. Such a functional protein can be directly or indirectly added to one or both of the N-terminal side and the C-terminal side of the nuclease. The functional protein is not particularly limited, and is selected as appropriate depending on a function to be provided to the nuclease. Examples thereof include a green fluorescent protein (GFP), a luciferase protein, a FLAG-tag protein (registered trademark, Sigma-Aldrich Co.), a glutathione-S-transferase (GST) protein for facilitating the detection or the like of the nuclease. Meanwhile, a nuclear localization signal may be added from the viewpoint that the nuclease stably functions in the nucleus.

Further, in the step (iii), the expression of the nuclease may be an expression induced in response to a stimulus, or may be a constitutive expression, but is preferably an expression induced in response to a stimulus. This is because the labor for the subsequent transformation can be omitted and the time can also be shortened, by using, as a plant cell into which the DNA construct of the present invention is introduced, a plant cell capable of inducibly expressing the nuclease in response to a stimulus, which is prepared and established in advance. Further, reducing the labor and time can reduce: the probability of natural mutation due to callus formation, the decrease in the re-differentiation efficiency dependent on the length of the culturing period, and so forth. Thus, the expression of the nuclease is preferably induced in response to a stimulus.

Furthermore, an example of the method for inducibly expressing the nuclease in the step (iii) includes a method in which a DNA construct comprising a gene encoding the nuclease and a regulatory region for inducibly expressing the gene is introduced into the plant cell followed by culturing in the presence of a stimulus, that is a condition for inducing the expression.

The timing of introducing the DNA construct for inducibly expressing the nuclease into the plant cell may be simultaneous with or before the introduction of the above-described DNA construct comprising the DNAs homologous to the target DNA in the step (i). Further, the timing may be before the selection based on the expression of the marker gene in the step (ii), or may be after the selection. From the above-described viewpoints, it is preferable to introduce the DNA construct before the step (i) to establish a plant cell capable of inducibly expressing the nuclease in response to a stimulus.

In addition, as the "regulatory region for inducibly expressing" the nuclease, it is possible to use the "regulatory regions for inducible expression" listed in the above description of "the DNA construct of the present invention." A promoter which induces the expression in response to β-estradiol is preferable from the viewpoint that the presence or absence of the expression can be strictly controlled in accordance with the presence or absence of the chemical treatment.

Figure 7:
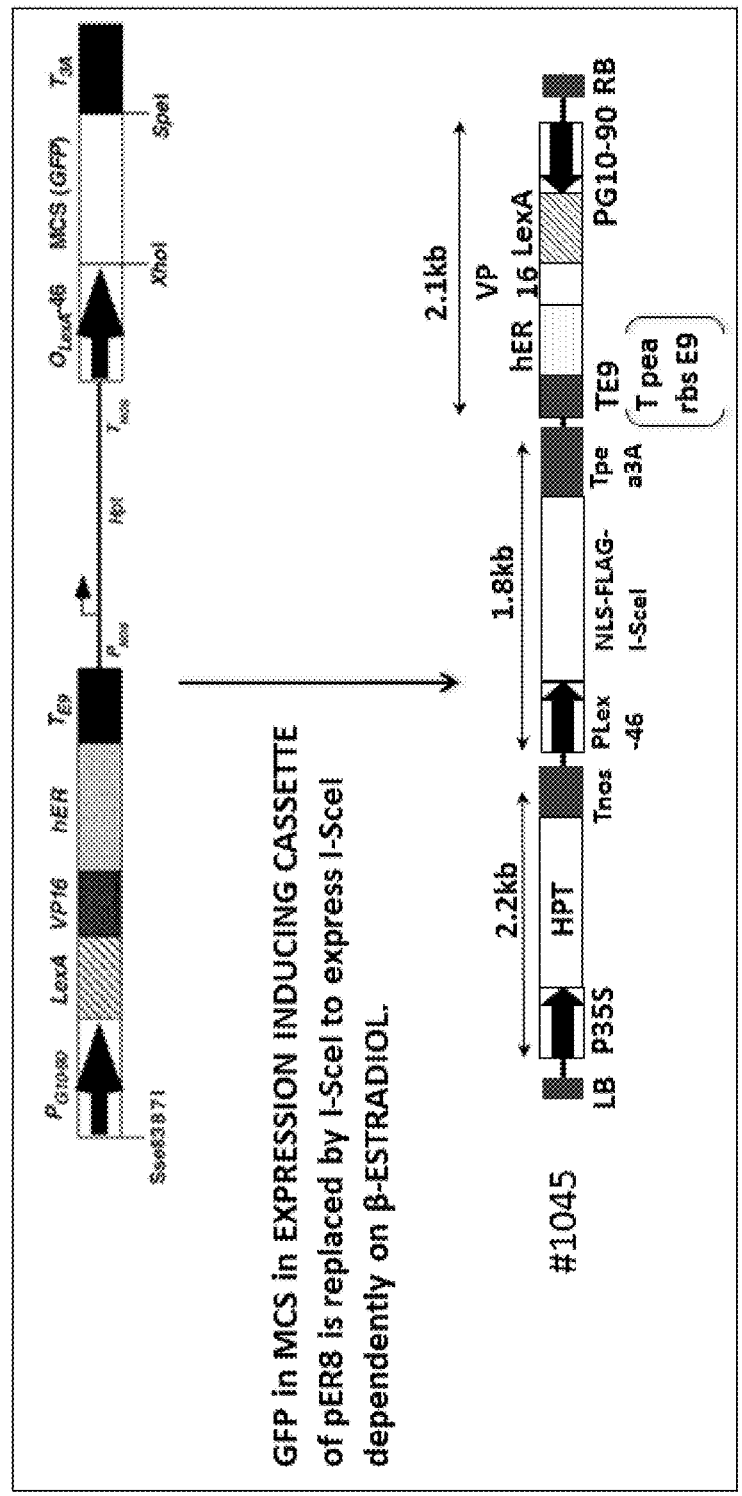
FIG. 7 is a schematic diagram showing a configuration of an I-SceI expression construct (#1045) introduced in a plant cell to inducibly express I-SceI in the cell in response to β-estradiol.

An example of such a promoter includes a promoter containing an LexA responsive sequence, which is activated by binding of β-estradiol and a synthetic transcription activator XVE, and in which a partial sequence of a repressor LexA of an *Escherichia coli* SOS regulon, a transcription activation domain of HSV (herpes simplex virus)-derived VP16, and an estrogen-receptor regulatory region (ER) are fused together (for example, PLex-46) (see FIG. 7) as described later in Examples.

On the other hand, the method for constitutively expressing the nuclease is not particularly limited. An example thereof include a method in which a DNA construct comprising a gene encoding the nuclease and a regulatory region for constitutively expressing the gene is introduced into the cell selected in the step (ii). Further, the DNA construct to be introduced is preferably inserted in the genomic DNA of the plant cell from the viewpoint that the nuclease is constitutively and stably expressed.

As the "regulatory region for constitutively expressing" the nuclease, it is possible to use the "regulatory regions for constitutive expression" listed in the above description of "the DNA construct of the present invention."

Further, the DNA construct for constitutively or inducibly expressing the nuclease may comprise the above-described reporter gene and chemical resistance gene because the plant cell, in which the DNA construct is introduced, can be efficiently selected.

In addition, the method for introducing the DNA construct for constitutively expressing the nuclease into plant cells is not particularly limited. It is possible to use various methods known to those skilled in the art such as an *Agrobacterium*-mediated method, a polyethylene glycol method, an electroporation method, and a particle gun method.

Then, the nuclease is expressed in the cell selected in the step (ii) as described above, so that the nuclease cleaves the first and second nuclease recognition sites, and the marker gene can be removed from the target DNA. Further, homologous recombination occurs between the short overlapping DNA sequences adjacent to the first and second nuclease recognition sites thus cleaved, and these nuclease recognition sites can also be removed. Consequently, in the method for introducing a mutation into a target DNA on the genome of a plant cell via homologous recombination, it is made possible to stably select a plant cell, in which the mutation is introduced, based on the expression of the marker gene. Further, it is also possible to remove an unnecessary sequence such as the marker gene in the selected cell, and to introduce only a required mutation into the target DNA (see FIG. 1).

Moreover, in the production method of the present invention, in order to improve the homologous recombination efficiency between the short overlapping DNA sequences, RecQl4 and/or Exo1 may be expressed together with the nuclease. Regarding RecQl4 and Exo1, see the description of NPL 2.

<Plant Cell>

As described above, the production method of the present invention makes it possible to obtain a plant cell comprising only a desired mutation introduced in a target DNA. Thus, the present invention provides a plant cell comprising a mutation introduced in a target DNA, and produced by the production method.

Moreover, as described later in Examples, the plant cell comprising the marker gene flanked by the first and second nuclease recognition sites and a desired mutation inserted in a target DNA via homologous recombination is one prepared for the first time in the present invention. This is useful in preparing a plant cell comprising only a desired mutation introduced in a target DNA, as described above.

Thus, the present invention also provides a plant cell comprising a marker gene flanked by first and second nuclease recognition sites, and the following mutation introduced in a target DNA via homologous recombination with a first DNA and a second DNA homologous to the target DNA by introducing a DNA construct comprising the marker gene and the first and second homologous DNAs, the DNA construct having the above-described features (a) to (d).

In the present invention, the term "plant" is not particularly limited. Examples thereof include monocot plants such as rice (*Oryza sativa*), wheat (*Triticum* spp.), barley (*Hordeum vulgare*), and corn (*Zea mays*); and dicot plants such as tobacco (*Nicotiana tabacum*), potato (*Solanum tuberosum*), eggplant (*Solanum melongena*), and rapeseed (*Brassica napus*). Moreover, the term "plant cell" includes cells in a plant, besides culture cells. Further, examples thereof include plant cells in various forms, for example, suspended culture cells, protoplasts, leaf sections, calli, immature embryos, pollens, and the like.

<Plant Etc.>

A plant can be obtained by regenerating the plant cell of the present invention. Particularly, since the plant cell produced by the production method of the present invention has only a desired mutation in a target DNA, a plant regenerated from such a plant cell has a phenotype changed by the mutation. Thus, utilization of the method of the present invention enables efficient plant breeding as well as efficient function analysis of the target DNA.

A plant can be regenerated from the plant cell by methods known to those skilled in the art in accordance with the type of the plant cell. An example for *Arabidopsis* includes the method described in Akama et al. (Plant Cell Reports 12: 7-11, 1992); for rice, examples include the methods described in Datta (In Gene Transfer To Plants (Potrykus I and Spangenberg Eds.) pp 66-74, 1995), Toki et al. (Plant Physiol. 100: 1503-1507, 1992), Christou et al. (Bio/technology, 9: 957-962, 1991), and Hiei et al. (Plant J. 6: 271-282, 1994); for barley, examples include the methods described in Tingay et al. (Plant J. 11: 1369-1376, 1997), Murray et al. (Plant Cell Report 22: 397-402, 2004), and Travalla et al. (Plant Cell Report 23: 780-789, 2005); for corn, examples include the methods described in Shillito et al. (Bio/Technology, 7: 581, 1989) and Gorden-Kamm et al. (Plant Cell 2: 603, 1990); for tomato (*Solanum lycopersicum*), an example includes the method described in Matsukura et al. (J. Exp. Bot., 44: 1837-1845, 1993); for soy bean (*Glycine max*), an example includes the method described in Patent Literature (U.S. Pat. No. 5,416,011); for potato, an example includes the method described in Visser et al. (Theor. Appl. Genet, 78: 594, 1989); and for tobacco, an example includes the method described in Nagata and Takebe (Planta, 99: 12, 1971). For plants other than those listed here, those skilled in the art can regenerate the plants by employing, for example, the methods described in "Protocols for Plant Transformation" edited by Tabei Yutaka (published by Kagaku-Dojin Publishing Company, INC.).

Once a plant comprising the cell comprising a mutation introduced in a target DNA is obtained as described above, a progeny can be obtained from the plant by sexual reproduction or asexual reproduction. Moreover, a propagation material (for example, a seed, a fruit, a spike, a stub, a callus, a protoplast, or the like) is obtained from the plant or a progeny or a clone thereof, from which mass production of the plant is also possible. Thus, the present invention includes: a plant comprising the plant cell of the present invention; a progeny and a clone of the plant; and a propagation material of the plant, the progeny, and the clone.

Meanwhile, although only a desired mutation is introduced in the target DNA of the plant cell produced by the production method of the present invention, the DNA encoding the exogenously-introduced nuclease generally remains in the cell. Nevertheless, crossing the plant comprising the plant cell produced by the production method of the present invention with a wild type plant and then backcrossing enable removal of the DNA encoding the nuclease, too.

Additionally, the present invention also provides a processed product produced from any of the plant cell, the plant, and the propagation material of the present invention. In the present invention, the processed product is not particularly limited, and refers to processed products in general, which have been conventionally produced from plants. Examples thereof include liquid extracts from plants, and plant dried powders and processed foods. More concretely, the examples include, in a case of rice, cooked rice, rice crackers, and the like; in a case of wheat, breads, noodles, and the like; in a case of corn, corn oil, corn starch, corn chips, and the like; in a case of soybean, soybean oil, tofu, natto, and the like; in a case of potato, potato chips, starches, and the like; in a case of tomato, ketchup and the like; and in a case of canola, canola oil and the like.

<Kit Etc.>

As described above, the DNA construct of the present invention is useful in the production method of the present invention, and the effectiveness is also demonstrated for the first time in the present invention. Thus, the present invention also provides a DNA construct comprising: a marker gene; and a first DNA and a second DNA homologous to a target DNA, the DNA construct having the above-described features (a) to (d).

In addition, as described above, a DNA construct for constitutively expressing a nuclease in a plant cell is also useful in the production method of the present invention. Thus, the present invention also provides a kit for use in the production method of the present invention, the kit comprising the following (A) and (B):

(A) a DNA construct comprising a marker gene, and a first DNA and a second DNA homologous to a target DNA, the DNA construct having the above-described features (a) to (d); and (B) a DNA construct for expressing in a plant cell a nuclease capable of specifically recognizing the first and second nuclease recognition sites.

Although each of these DNA constructs is as described above in the steps (i) and (iii) of the production method of the present invention, the form thereof may be a single-stranded DNA or a double-stranded DNA. Alternatively, the form may be a linear DNA or a circular DNA, and the DNA constructs can be prepared in a form suitable for the above-described introduction method into a plant cell.

For example, when *Agrobacterium* is used for the introduction into a plant cell, examples of the form of the DNA constructs include pBI-based, pPZP-based, or pSMA-based vectors, and other similar vectors. Moreover, examples of amore preferable form include vectors of binary vector systems (such as pZHG, pKOD4, pBI121, pBI101, pBI101.2, pBI101.3, pBIG2113).

Meanwhile, for the introduction into a plant cell by other methods such as an electroporation method, examples of the form of the DNA construct include pUC-based vectors such as pUC18, pUC19, and pUC9. Further, the DNA constructs may take a form of a plant virus vector such as CaMV, bean golden mosaic virus (BGMV), or tobacco mosaic virus (TMV).

Moreover, those skilled in the art can prepare such DNA constructs as appropriate by utilizing known genetic recombination techniques such as a PCR method, a restriction enzyme treatment, and a cloning method as described later in Examples. Additionally, the DNA constructs can also be chemically synthesized by using a commercially-available automated DNA sequence synthesizer or the like.

Further, in preparing the DNA construct according to (A), those skilled in the art can introduce a desired mutation into the DNA homologous to a target DNA by site-directed mutagenesis (for example, the method described in Kunkel, TA (1985) Proc Natl Acad Sci USA. 82, 488-492) or the like.

In addition, from the viewpoint of expressing the nuclease in a plant cell at a high level, a DNA encoding the nuclease optimized for a codon usage frequency of a plant, into which the DNA construct is introduced, may be inserted in the DNA construct according to (B).

EXAMPLES

Hereinafter, the present invention will be more specifically described on the basis of Examples and Reference Example. However, the present invention is not limited to the following Examples.

In gene targeting (GT, the method for introducing a mutation into a target DNA on the genome of a plant cell via homologous recombination), the present inventors have come up with the idea of the system shown in FIG. 1 for enabling: stable selection of a plant cell, in which mutation is introduced, based on an expression of a marker gene; the subsequent removal of an unnecessary sequence such as the marker gene from the selected cell; and the introduction of only a required mutation into the target DNA.

To be more specific, first, as shown in the first step in FIG. 1, homologous recombination is allowed to occur by introducing into plant cells a DNA construct comprising: a marker gene (positive selectable marker gene); and a first DNA and a second DNA homologous to a target DNA.

Note that, in this DNA construct, (a) the first homologous DNA is added to a 5' side of the marker gene via a first nuclease recognition site, (b) the second homologous DNA is added to a 3' side of the marker gene via a second nuclease recognition site, (c) a 3' end region of the first homologous DNA and a 5' end region of the second homologous DNA are DNA sequences having 30 to 500 nucleotides (short overlapping DNA sequences) homologous to each other, and (d) in at least one DNA of the first homologous DNA and the second homologous DNA, a desired mutation is introduced in a region other than the short overlapping DNA sequence.

As a result of the homologous recombination between the target DNA on the genomic DNA of a plant cell and the first and second homologous DNAs, the mutation and the marker gene flanked by the first and second nuclease recognition sites are introduced in the target DNA.

Moreover, in this event, disposing a negative selectable marker gene outside the homologous DNAs eliminates cells in which the DNA construct is randomly inserted in a region other than the target DNA.

Then, the plant cell, in which the mutation and so forth are introduced in the target DNA, is selected by screening based on an expression of the marker gene.

Further, as shown in the second step in FIG. 1, a nuclease capable of specifically recognizing the first and second nuclease recognition sites is expressed in the cell selected as described above. The nuclease cleaves the first and second nuclease recognition sites, and the marker gene is removed from the target DNA. Further, homologous recombination occurs between the short overlapping DNA sequences adjacent to the first and second nuclease recognition sites thus cleaved, and these nuclease recognition sites are also removed.

Thus, according to this idea, it is possible to prepare a mutant plant having only a desired mutation in a target DNA.

Hence, the system shown in FIG. 1 was constructed to verify the effectiveness by the method described below. Note that, as the target DNA and the mutation introduced into the DNA in the present Examples, a rice phytoene desaturase (PDS) gene and an R304S mutation (CGA->AGT) were selected, respectively. In addition, I-SceI was selected as the nuclease, while an NPTII gene and a DT-A (diphtheria toxin a subunit) gene were selected as the positive selectable marker gene and the negative selectable marker gene, respectively.

Example 1

<Construction of Gene Targeting (GT) Vector>

A GT vector (positive-negative selection vector) targeting the PDS locus was constructed as follows.

In the construction, first, a PDS genome sequence upstream of the positive selectable marker gene was cloned. To be more specific, a genomic DNA was prepared from rice (cultivar: Nipponbare) by the method described in "Endo M. et al., Plant J., 2007, Vol. 52, pp. 157 to 166." Using the genomic DNA as a template, the second PCR was carried out. The PCR product was cloned into a pCR-Blunt II-TOPO vector (manufactured by Life Technologies Corporation). After the PacI recognition site in the PCR product was replaced by the HpaI recognition site using QuikChange II XL Site-Directed Mutagenesis Kit (manufactured by Agilent Technologies), the PCR product was excised utilizing the AscI recognition site and the PacI recognition site, and cloned into pE (L1-L4) having been similarly treated with AscI and PacI. The primers used in the PCR were as follows.

```
<1st PCR>
AscPDS 4.7kF
                                        (SEQ ID NO: 1)
5'-ttctggcgcgccTGCATGAGGAGGCAAACGAGGTCCT-3'

I-SceI PDS 7.3kR
                                        (SEQ ID NO: 2)
5'-ACCCTGTTATCCCTAGCTTAAACCTGTGCAAAAGGATCTGGGCA-3'

<2nd PCR>
AscPDS4.7kF
                                        (SEQ ID NO: 3)
5'-ttctggcgcgccTGCATGAGGAGGCAAACGAGGTCCT-3'

PacI-SceI PDS 7.3kR
                                        (SEQ ID NO: 4)
5'-GAAGTTAATTAATTACCCTGTTATCCCTAGCTTAAACCT-3'.
```

Next, a PDS genome sequence downstream of the positive selectable marker gene was cloned. To be more specific, using the above-described rice (cultivar: Nipponbare) genomic DNA as a template, the second PCR was carried out. The PCR product was cloned into a pCR-Blunt II-TOPO vector (manufactured by Life Technologies Corporation). After the R304S mutation (CGA->AGT) was introduced into the PCR product using QuikChange II XL Site-Directed Mutagenesis Kit (manufactured by Agilent Technologies), the PCR product was excised utilizing the AscI recognition site and the PacI recognition site, and cloned into pE (L3-L2) having been similarly treated with AscI and PacI. The primers used in the PCR were as follows.

```
<1st PCR>
I-SceI PDS 7.3kF
                                        (SEQ ID NO: 5)
5'-ACCCTGTTATCCCTATGCCCAGATCCTTTTGCACAGGTTTAAGCT-
3'

Pac PDS 10kR
                                        (SEQ ID NO: 6)
5'-ATTGTTAATTAAagtgagtgcaaagggagaTAAGGTCTCT-3'

<2nd PCR>
Asc I-SceI PDS 7.3kF
                                        (SEQ ID NO: 7)
5'-AATTGGCGCGCCATTACCCTGTTATCCCTATGCCCAGATCCT-3'

Pac PDS 10kR
                                        (SEQ ID NO: 6)
5'-ATTGTTAATTAAagtgagtgcaaagggagaTAAGGTCTCT-3'.
```

Then, using LR Clonase II Plus (registered trademark, manufactured by Life Technologies Corporation), pKDO4, pE(L1-L4)PDS5', pE(R4-R3)TacP35SnptIIThsp17.3, and pE(L3-L2)PDS3' were linked to each other. Thus, a GT vector was constructed.

Figure 2:
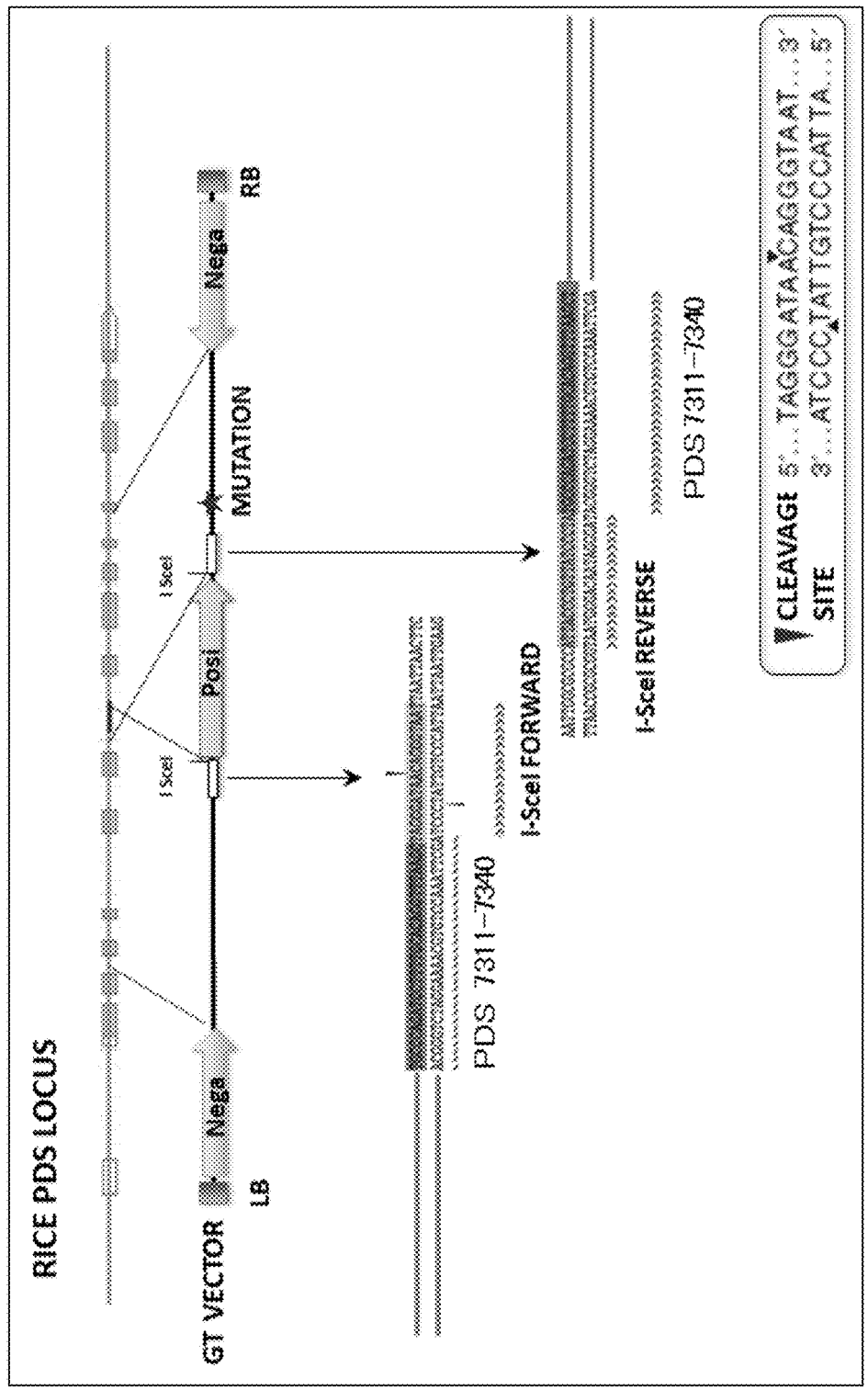
FIG. 2 is a schematic representation for illustrating a mode of the method for producing a plant cell of the present invention, when the target DNA is a rice PDS locus, and the nuclease is I-SceI. To be more specific, the schematic diagram illustrates that: SEQ ID NO: 22 (5'-tgcccagatc cttttgcaca ggtttaagct agggataaca gggtaattaa ttaacttc-3') includes a short overlapping DNA sequence (PDS 7311 to 7340 (SEQ ID NO: 8), 30 nucleotides), which is homologous to a region having nucleotides 7311 to 7340 of the PDS gene, is added to a 5' side of the positive selectable marker gene via a first nuclease recognition site (I-SceI forward (SEQ ID NO: 9), 18 nucleotides); SEQ ID NO: 24 (5'-aattggcgcg ccattaccct gttatcccta tgcccagatc cttttgcaca ggtttaagc -3') includes a short overlapping DNA sequence (PDS 7311 to 7340 (SEQ ID NO: 8), 30 nucleotides), which is homologous to the region having nucleotides 7311 to 7340 of the PDS gene, is added to a 3' side of the marker gene via a second nuclease recognition site (I-SceI reverse (SEQ ID NO: 10), 18 nucleotides); and the first nuclease recognition site and the second nuclease recognition site are disposed in directions opposite to each other. In the figure, cleavage sites of I-SceI are indicated by arrow heads, and the specific cleavages are shown at the bottom of the figure. SEQ ID NO: 23 (5'-gaagttaatt aattaccctg ttatccct agcttaaacc tgtgcaaaag gatctgggca -3') is complementary to SEQ ID NO: 22, and SEQ ID NO: 25 (5'-agcttaaacc tgtgcaaaag gatctgggca tagggataac agggtaatgg cgcgccaatt-3') is complementary to SEQ ID NO: 24.

In the GT vector constructed as described above, 18-bp I-SceI recognition sequences are present at both ends of the positive selectable marker gene (NPTII gene). For this reason, when I-SceI is expressed in aplant cell transformed using the GT vector to have the gene introduced in the PDS locus (target DNA) as shown in FIG. 1, the I-SceI sequences are cleaved, and the positive selectable marker gene is removed from the target DNA. Nevertheless, if the two I-SceI recognition sites are simply utilized to excise the positive selectable marker gene, broken ends are rejoined, leaving the I-SceI recognition site as they are. Hence, the GT vector is devised as follows. Concretely, 30-bp overlapping rice genome sequences are formed in regions adjacent to the I-SceI recognition sites as shown in FIG. 2, and homologous recombination is allowed to occur between the short overlapping DNA sequences (PDS 7311-7340) at the broken ends after the marker gene is removed, enabling the removal of the positive selectable marker without leaving any trace. Further, in the GT vector, the I-SceI recognition site disposed adjacent to the 5' end side of the positive selectable marker gene and the I-SceI recognition site disposed adjacent to the 3'end side thereof are oriented in directions opposite to each other as shown in FIG. 2. This is because if these I-SceI recognition sites are oriented in the same direction, when the sites are cleaved by I-SceI, end sequences resulting from the cleavage are likely to rejoin, so that the homologous recombination between the above-described short overlapping DNA sequences is unlikely to occur.

Note that SEQ ID NOs: 8 to 10 respectively show the short overlapping DNA sequence "PDS 7311-7340" and the sequences of the I-SceI recognition sites "I-SceI forward" and "I-SceI reverse" shown in FIG. 2.

Example 2

Next, the GT vector was used to prepare a plant having only a desired mutation in a target DNA by the method described below.

To be more specific, first, the GT vector was introduced into an *Agrobacterium* strain EHA105 by an electroporation method. Then, the rice transformation was carried out by the method (*Agrobacterium* method) described in "Toki S., Plant Mol. Biol. Rep., 1997, Vol. 15, pp. 16 to 21" and "Toki S. et al., Plant J., 2006, Vol. 47, pp. 969 to 976." More concretely, rice seeds (cultivar: Nipponbare) were sterilized and placed on a callus induction medium. After 3 weeks of culturing, formed calli were infected with *Agrobacterium* having the above-described GT vector. After the rice calli and the *Agrobacterium* were co-cultured, the *Agrobacterium* was eliminated. Subsequently, the rice calli were placed on selection media (N6D solidified media supplemented with 35 mg/L of G418) to select GT candidate calli (G418-tolerant calli). Table 1 to be described later shows the obtained result.

Note that, in the culturing on the selection media, cells not transformed with the GT vector exhibit G418 sensitivity and do not grow. Cells transformed with the GT vector which is, however, randomly inserted in the rice genome cannot grow due to the negative selectable marker diphtheria toxin a subunit (DT-A). Thus, calli in which GT successfully occurred grow on the selection media.

Figure 3:
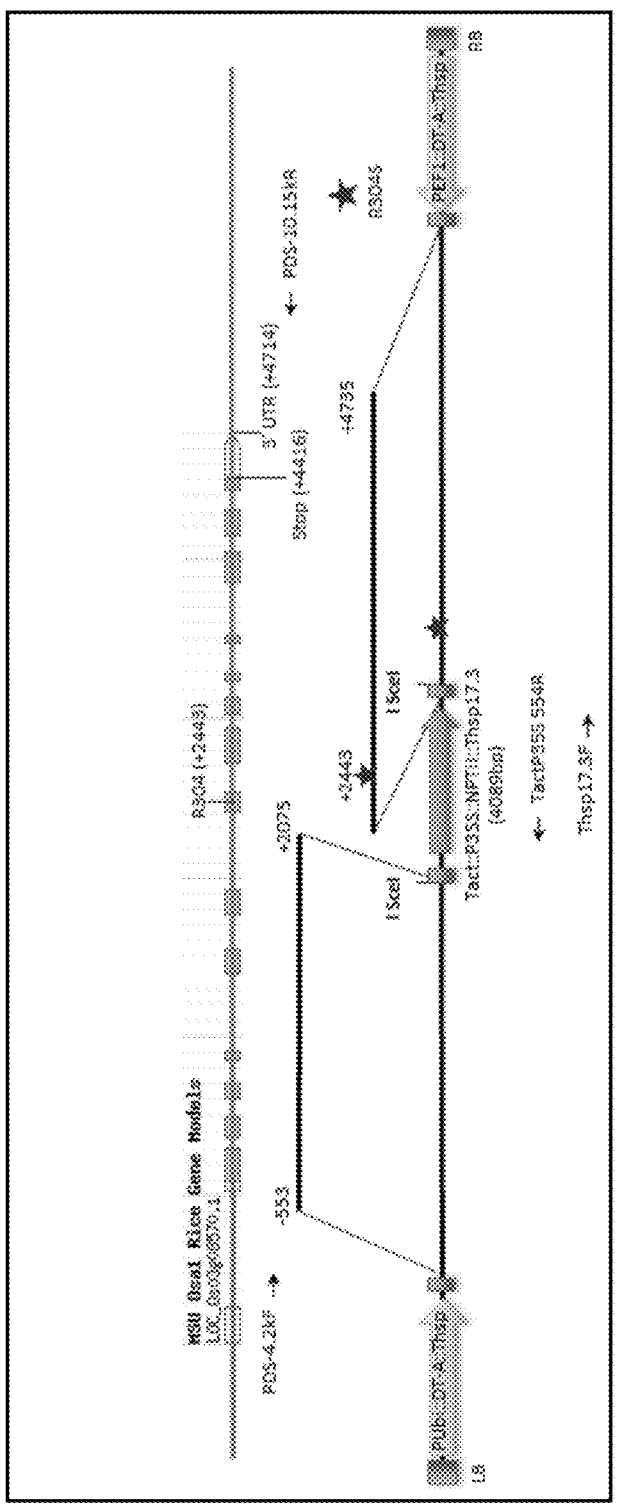
FIG. 3 is a schematic diagram of a PCR analysis targeting plant cells (GT candidate calli) selected in a step (ii) of the method for producing a plant cell of the present invention. The PCR analysis was carried out to examine whether or not the marker gene was inserted in the target DNA (PDS locus).
Figure 4:
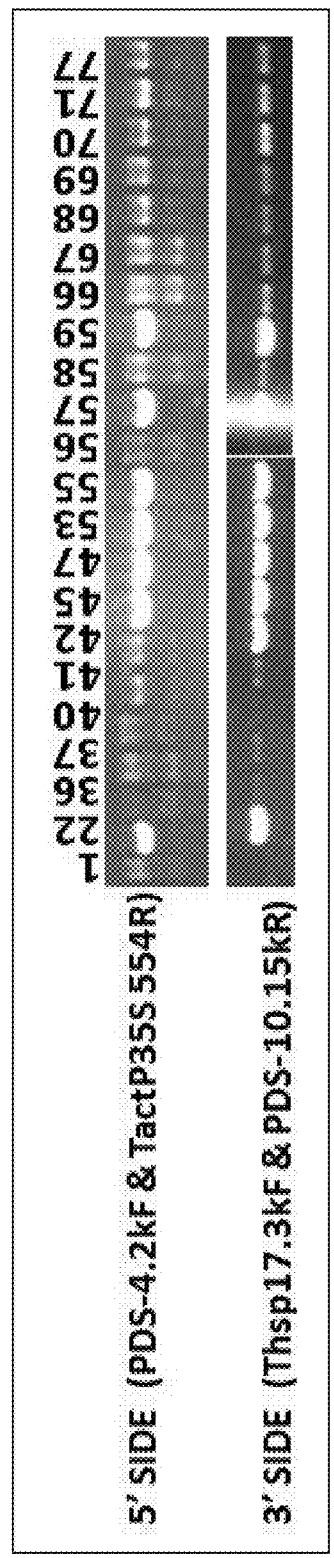
FIG. 4 shows photographs of gel electrophoresis for illustrating the result of the PCR analysis shown in FIG. 3.

Next, genomic DNAs were prepared from the calli grown on the media supplemented with G418 to confirm by PCR that the positive selectable marker gene was inserted in the target DNA (PDS locus) of these calli. When the GT successfully occurs, the positive selectable marker gene is inserted in the sixth intron of the PDS. For this reason, the PCR was performed using a forward primer (Thsp17.3F) to be positioned on the positive selectable marker gene and a reverse primer (PDS-10.15kR) to be positioned downstream of a PDS downstream gene not included on the GT vector. Further, the PCR was performed using a reverse primer (TactP35S554R) to be positioned on the positive selectable marker gene and a forward primer (PDS-4.2kR) to be positioned upstream of the PDS not included on the GT vector (see FIG. 3). Table 1 to be described later shows the obtained result. In addition, FIG. 4 shows some examples of the result. Note that, with these combinations of the primers, the randomly inserted GT vector is not amplified, while the PCR product is amplified only when the positive selectable marker gene is inserted in the endogenous PDS locus by GT. Additionally, the sequences of the primers used were as follows.

```
Thsp17.3F
                                                (SEQ ID NO: 11)
5'-ACATACCCATCCAACAATGTTCAATCCCTT-3'
```

```
-continued
PDS-10.15kR
                                                (SEQ ID NO: 12)
5'-TGGATTTGTAGAGTTAGAAATACCTGACTT-3'

PDS-4.2kF
                                                (SEQ ID NO: 13)
5'-TGATGGACTGATTGGCTGATGGTGGT-3'

TactP35S 554R
                                                (SEQ ID NO: 14)
5'-CTGACGATGAGAATATATCTGATGCTGTGA-3'.
```

Figure 5:
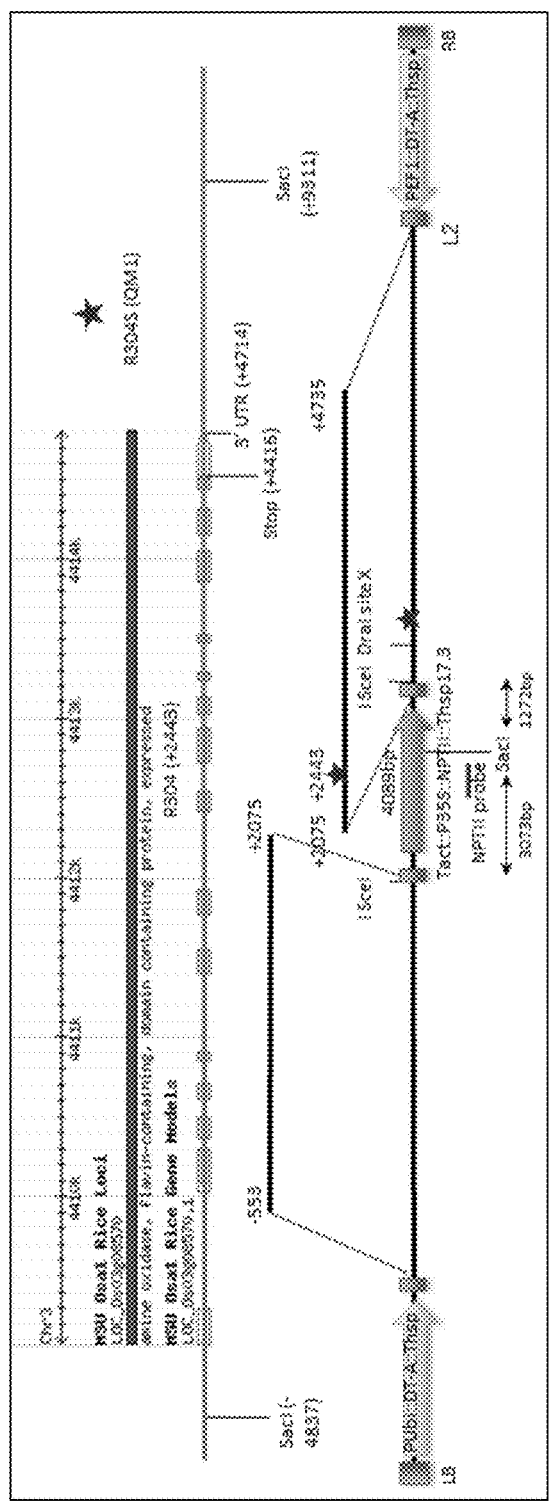
FIG. 5 is a schematic diagram of a Southern blotting analysis targeting the plant cells (GT candidate calli) selected in the step (ii) of the method for producing a plant cell of the present invention, and confirmed to have the marker gene inserted by the PCR shown in FIG. 3. The Southern blotting analysis was carried out to examine whether the insertion was due to homologous recombination or random insertion.
Figure 6:
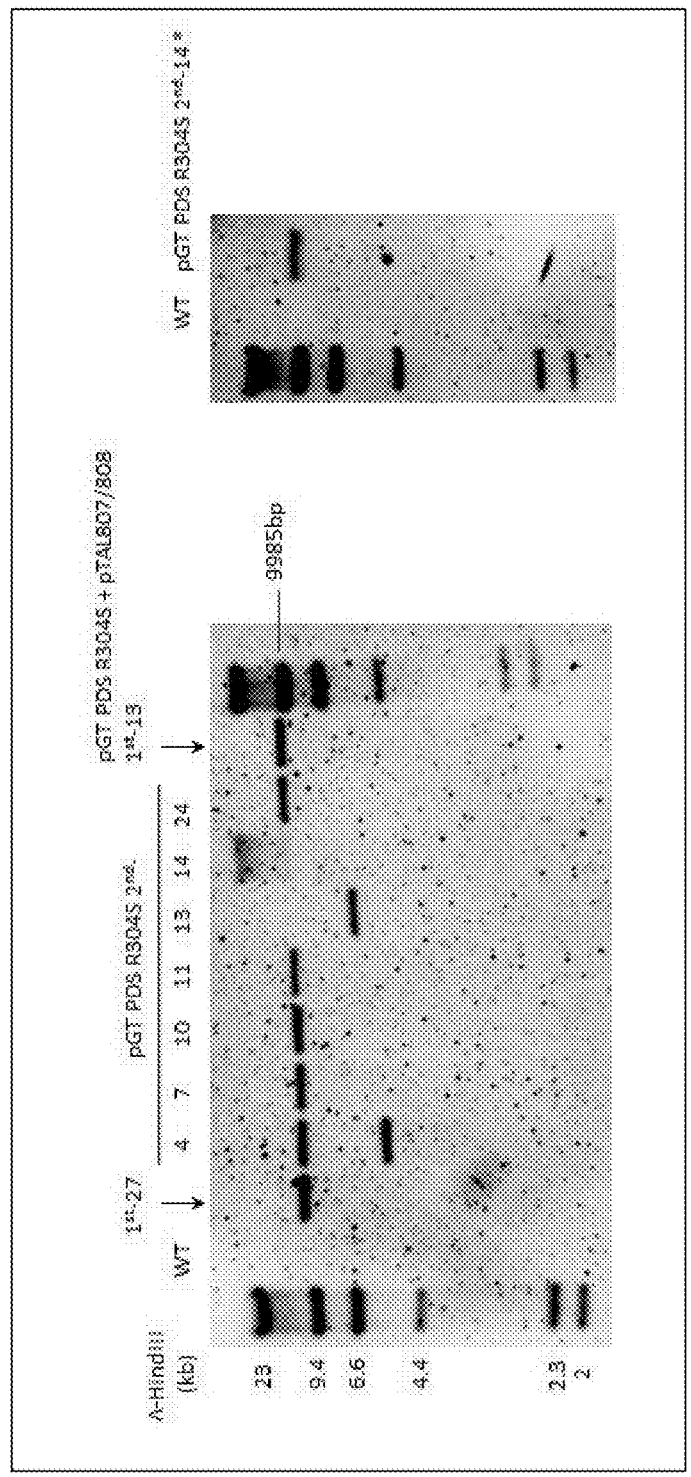
FIG. 6 shows photographs of membranes for illustrating the result of the Southern blotting analysis shown in FIG. 5. Note that, in the figure, representations other than WT (wild type rice) show the analysis result of the GT candidate calli. Moreover, in this Southern blotting analysis, only a band of 9985 bp is detected when homologous recombination has occurred. Bands other than 9985 bp suggest random insertion of the GT vector with the negative selectable marker gene eliminated.

Further, the GT was confirmed by a Southern blotting method (see FIG. 5). To be more specific, the genomic DNAs were extracted from the GT cells identified by the above-described PCR. The DNAs were treated with SacI for the detection using a probe to be positioned on the NPTII gene as the positive selectable marker gene. Table 1 and FIG. 6 show the obtained result. Note that the Southern blotting was performed according to the method described in "Endo M. et al., Plant J., 2007, Vol. 52, pp. 157 to 166." In addition, the primers used in the preparation of the probe (DIG probe) used for the detection and the sequences of the primers were as follows.

```
                                                (SEQ ID NO: 15)
nptII + 23Fw     5'-TTGAACAAGATGGATTGCAC-3'

(SEQ ID NO: 16)
nptII + 527Rv    5'-GGCATCGCCATGTGTCACGA-3'.
```

TABLE 1

|  | The number of calli tested | Posi-nega selection | GT |
|---|---|---|---|
| Experiment 1 pGT PDS R304S | 706 | 28 | 1 |
| Experiment 2 pGT PDS R304S | 734 | 27 | 7 |
| Total | 1440 | 55 | 8 (0.6%) |

As shown in Table 1, the above-described transformation experiment was conducted twice. A total of 1440 calli were used in the GT vector transformation, and 55 G418-tolerant calli were obtained. Then, DNAs were prepared from these 55 G418-tolerant calli, and subjected to the above-described PCR for amplifying the product only when the GT occurred in the PDS locus. As a result, the amplification was observed in 11 calli.

Further, the GT in the 11 calli was checked by the Southern blotting analysis, followed by the detection using the probe to be positioned on the positive selectable marker gene. As a result, a band of approximately 10 kb, which appears when GT occurs, was detected in eight calli (GT calli) as shown in Table 1 and FIG. 6. Thus, the GT efficiency was 0.6% (8/1440) in relation to the tested callus, and 14.5% (8/55) in relation to the calli obtained by the positive-negative selection.

Next, I-SceI was expressed in the above-described calli in which the GT in the target DNA was confirmed. The positive selectable marker gene was removed from the target DNA.

Figure 8:
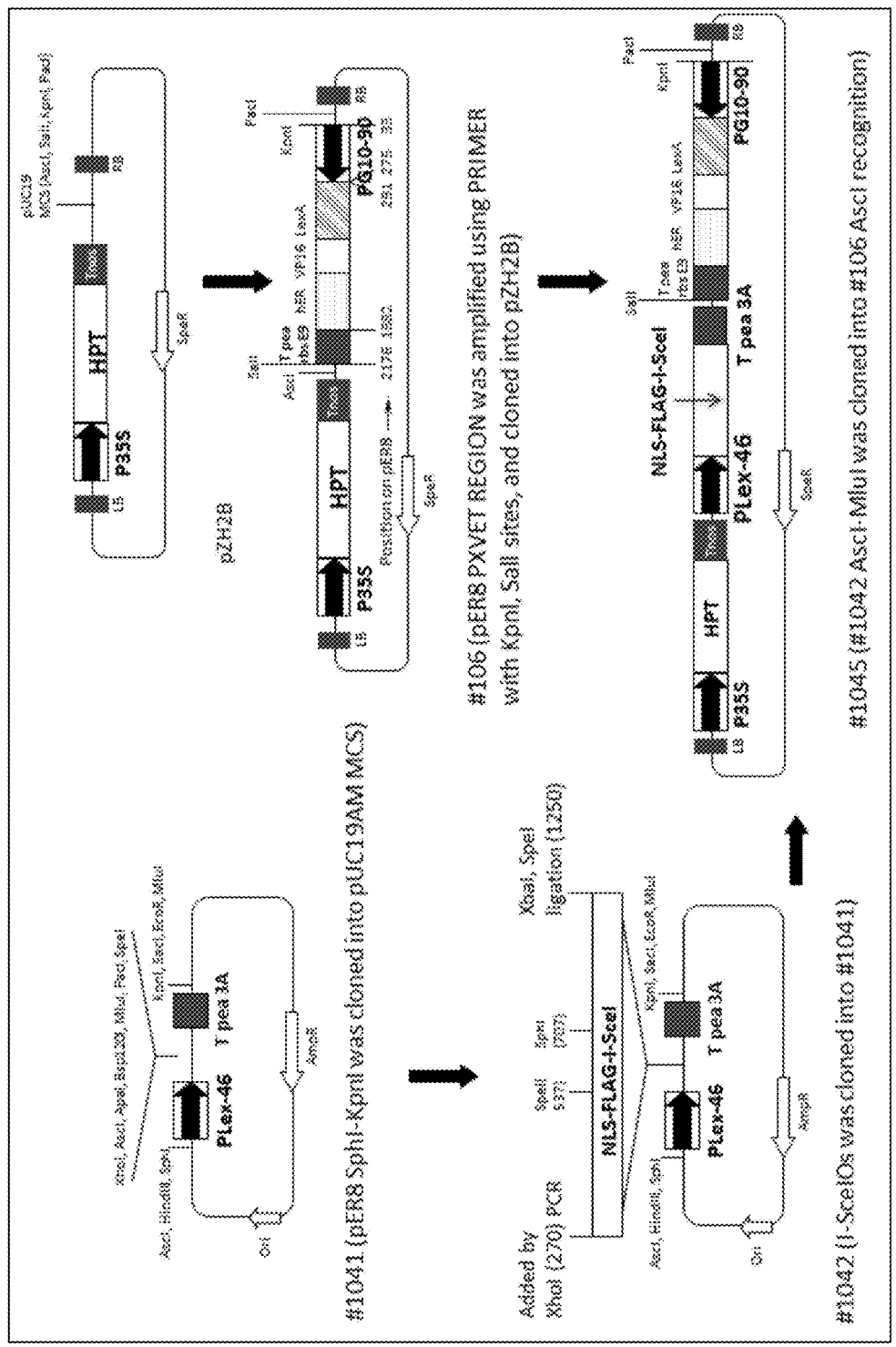
FIG. 8 is a schematic diagram for illustrating the steps for preparing #1045.

In the removal, first, in order to inducibly express I-SceI in the calli in response to a stimulus (β-estradiol), an I-SceI expression construct (#1045, see FIG. 7) was prepared according to steps shown in FIG. 8. To be more specific, to construct the vector (#1045) for expressing I-SceI in a manner dependent on β-estradiol by replacing a DNA encoding GFP in the multicloning site (MCS) of pER8 (see Zuo J. et al., Plant J., 2000, Vol. 24, pp. 265 to 273) by a DNA encoding I-SceI, first, the sequence between PLex-46 and Tpea3A in the pER8 was replaced by the sequence between a SphI recognition site and a KpnI recognition site in pUC19AM (a vector in which an AscI recognition site and a PacI recognition site were added to both ends of the MCS of pUC19) to thus prepare a vector (#1041). Next, NLS-FLAG-I-SceI was cloned into an XhoI recognition site and a SpeI recognition site located between PLex-46 and Tpea3A to thus prepare #1042. Moreover, the sequence between PG10-90 and Tpea rbs E9 in the pER8 was cloned into a SalI recognition site and a KpnI recognition site of a binary vector pZH2B (see Kuroda M. et al., Biosci Biotechnol Biochem, 2010, Vol. 74, No. 11, pp. 2348 to 2351) to thus prepare #106. Then, the sequence between an AscI recognition site and an MluI recognition site of #1042 was cloned between an AscI recognition site and the SalI recognition site of #106 to thus prepare #1045. Note that the I-SceI gene (see Puchta H. et al., Nucleic Acids Res., 1993, Vol. 21, Iss. 22, pp. 5034 to 5040) used is a gene kindly provided from Puchta et al.

Next, in order to remove the positive selectable marker gene from the calli of the GT-induced generation, the eight GT calli in which the GT was confirmed as described above were infected with *Agrobacterium* having #1045. Then, the resultant was cultured for 2 weeks on N6D solidified media supplemented with hygromycin for the selection of #1045-transformed cells. Note that the transformation was carried out as in the above-described transformation using the GT vector.

Next, the GT calli transformed with #1045 were transferred to N6D solidified media supplemented with 5 μM β-estradiol to induce the I-SceI expression. The calli were cultured on the media for 2 weeks. After the growth and the I-SceI expression induction, the resultant was transferred to re-differentiation media not supplemented with β-estradiol to regenerate plants from the calli. As a result, 95 re-differentiated individuals were obtained.

Next, to analyze whether or not the positive selectable marker gene was removed from the target DNA by expressing I-SceI in the obtained re-differentiated individuals, PCR for amplifying a fragment containing the positive selectable marker gene was carried out using genomic DNAs extracted from these re-differentiated individuals as a template, and using the following primers.

```
                                    (SEQ ID NO: 17)
PDS-6.2kF    5'-AGGTAGAAATGCCATGCGGGAAGT-3'

(SEQ ID NO: 18)
PDS-8.33kR   5'-TCCGACTTGGAACCAAATAATTCA-3'.
```

Note that, in this PCR, approximately 6 kb of the PCR product is yielded if the positive selectable marker gene remains in the PDS locus. Meanwhile, approximately 2 kb of the PCR product is yielded from the wild type PDS locus and the PDS locus from which the positive selectable marker gene is removed after the GT.

Further, the sequences of the PCR products of calli from which the positive selectable marker gene was removed conceivably by the PCR were identified by direct sequencing. Note that, in the direct sequencing of the PCR product of an individual from which the marker gene is removed without any trace via homologous recombination, double peaks appear only at the site where the point mutation (R304S mutation (CGA->AGT)) is introduced. In cases where the short overlapping DNA sequences overlap and remain, and where a base is inserted or deleted, there will be two waveforms because of the presence of the PCR product derived from the wild type locus. Hence, the PCR product having two waveforms was cloned into a pCR-Blunt II-TOPO vector (manufactured by Life Technologies Corporation) for the sequencing analysis. Table 2 shows the obtained result. In the sequencing analysis, a primer (PDS-7.2kF) to be positioned upstream of the positive selectable marker was used. The sequence of the primer was as follows.

```
                                    (SEQ ID NO: 19)
PDS-7.2kF    5'-TCACATTGGGAAGAACTGGCAGT.
```

TABLE 2

| Re-differentiated individuals with the I-SceI expression vector introduced therein | Individuals from which the positive selectable marker was removed | | |
|---|---|---|---|
| | no trace | overlapping sequences remained | With insertion/deletion |
| 95 | 9 (9.5%) | 3 (3%) | 1 (1%) |

Then, as a result of the direct sequencing and the sequencing analysis on the cloned PCR product as shown in Table 2, nine plant individuals were identified which comprised the R304S mutation, but from which the positive selectable marker was neatly removed via homologous recombination, and from which the neatly linked sequence was detected with no base insertion or deletion and no short overlapping DNA sequences overlapping and remaining even partially (see "no trace" in Table 2). Besides, there were three individuals in which the short overlapping DNA sequences partially overlapped and remained, and there was one individual in which a different sequence from the short overlapping DNA sequences was inserted (see "overlapping sequences remained" and "with insertion/deletion" in Table 2)

Figure 9:
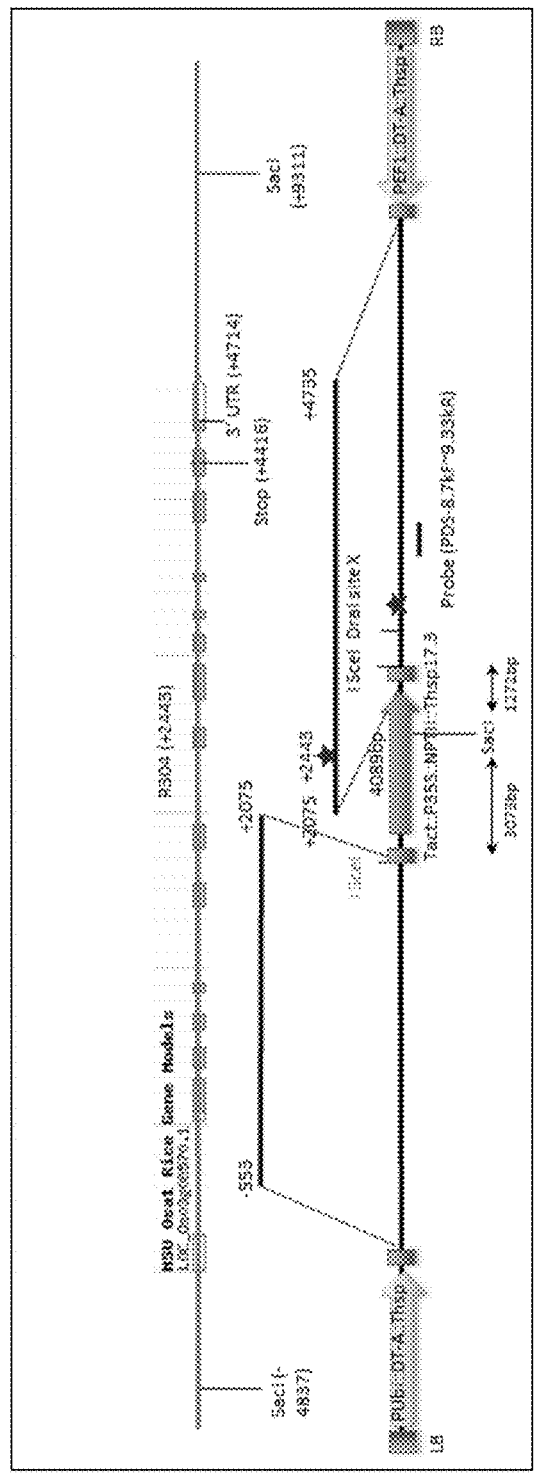
FIG. 9 is a schematic diagram of a Southern blotting analysis carried out to examine whether or not the positive selectable marker was removed by expressing I-SceI in the plant cells (GT calli) confirmed to have the marker gene inserted in the target DNA via the homologous recombination.
Figure 10:
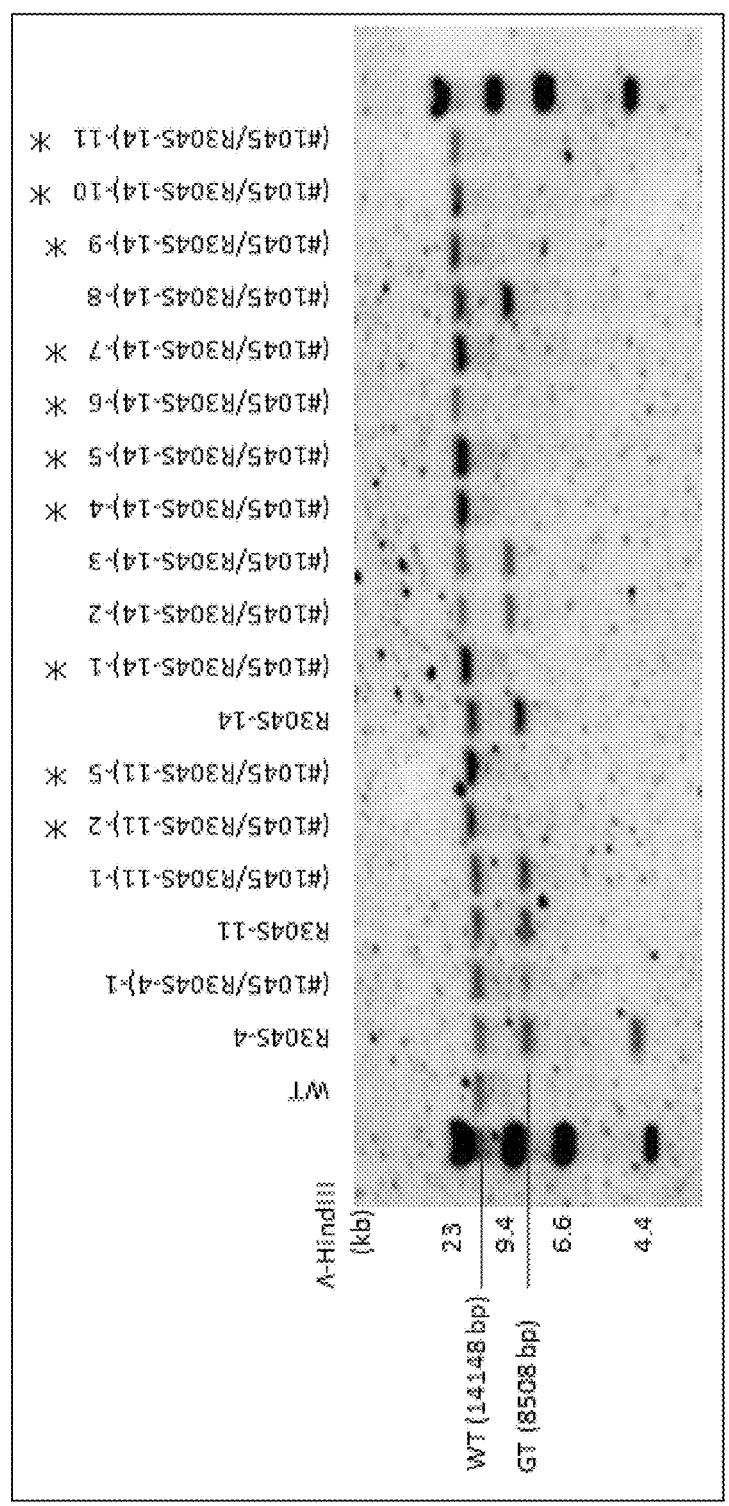
FIG. 10 is a photograph of a membrane for illustrating the result of the Southern blotting analysis shown in FIG. 9. In the figure, "WT" shows the analysis result of the wild type rice, while "R304S-4", "R304S-11", and "R304S-14" show the results of analyzing the GT calli before the #1045 transformation. The other representations show the results of analyzing re-differentiated individuals obtained by treating #1045 transformants with β-estradiol. Moreover, individuals provided with asterisks are individuals from which the marker gene was removed, while individuals provided with no sign are individuals in which the marker gene remained. Note that, regarding the representations in the figure, the same shall apply also to FIG. 12.

Further, a Southern blotting analysis shown in FIG. 9 was performed using the DNAs of the plants which were revealed that the positive selectable marker was removed without any trace. If the marker is removed without any trace after the GT, only the point mutation remains in the PDS locus. To be more specific, genomic DNAs were extracted from the plants and treated with SacI. Then, these treated products were fractionated by electrophoresis. The Southern blotting analysis was performed using the PDS gene as a probe, and confirmed that the band patterns were the same as that of the wild type. FIG. 10 shows the obtained result. Note that the primers used in the preparation of the DIG probe used for the detection were as follows.

```
                                    (SEQ ID NO: 20)
PDS-8.7kF    5'-TGCAAGGTACTAACTAGGAGACATT-3'

(SEQ ID NO: 21)
PDS-9.33kR   5'-TTGTAAACAGATCTGTAACAGTGA-3'.
```

As shown in FIG. 10, as a result of the Southern blotting analysis, the individuals, which were confirmed by the sequencing analysis on the PCR products that the marker was removed without any trace, exhibited the same band patterns as that of the wild type. Meanwhile, the individuals with the marker unremoved exhibited the same band patterns as that of the GT callus before the #1045transformation.

Figure 11:
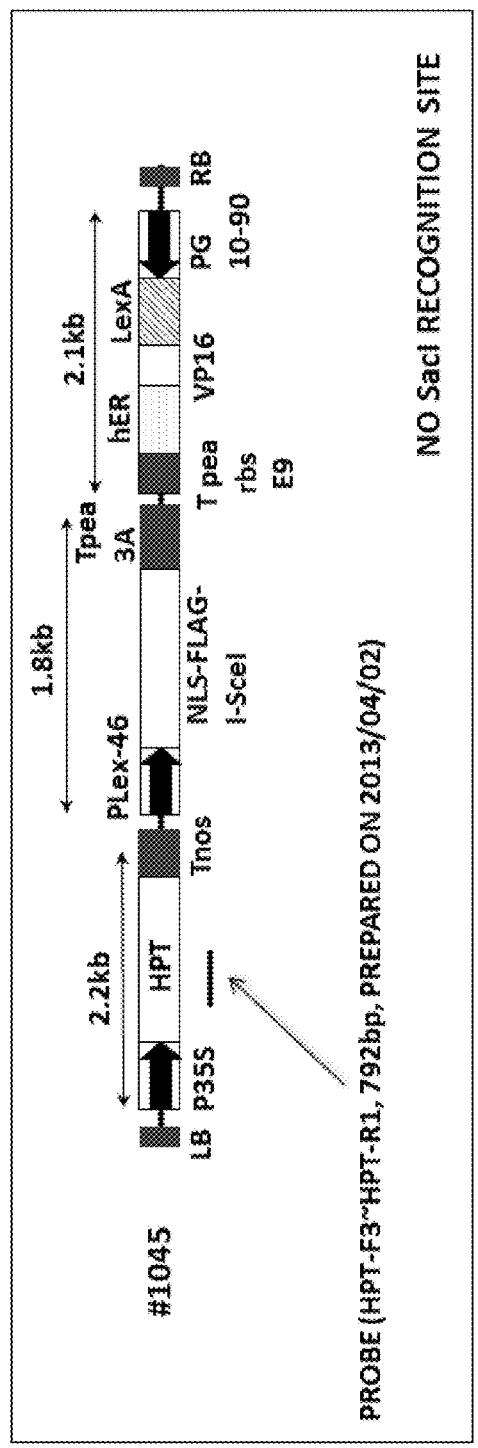
FIG. 11 is a schematic diagram of a Southern blotting analysis carried out using a probe targeting #1045to examine whether or not the marker gene was removed by expressing I-SceI in the GT calli.
Figure 12:
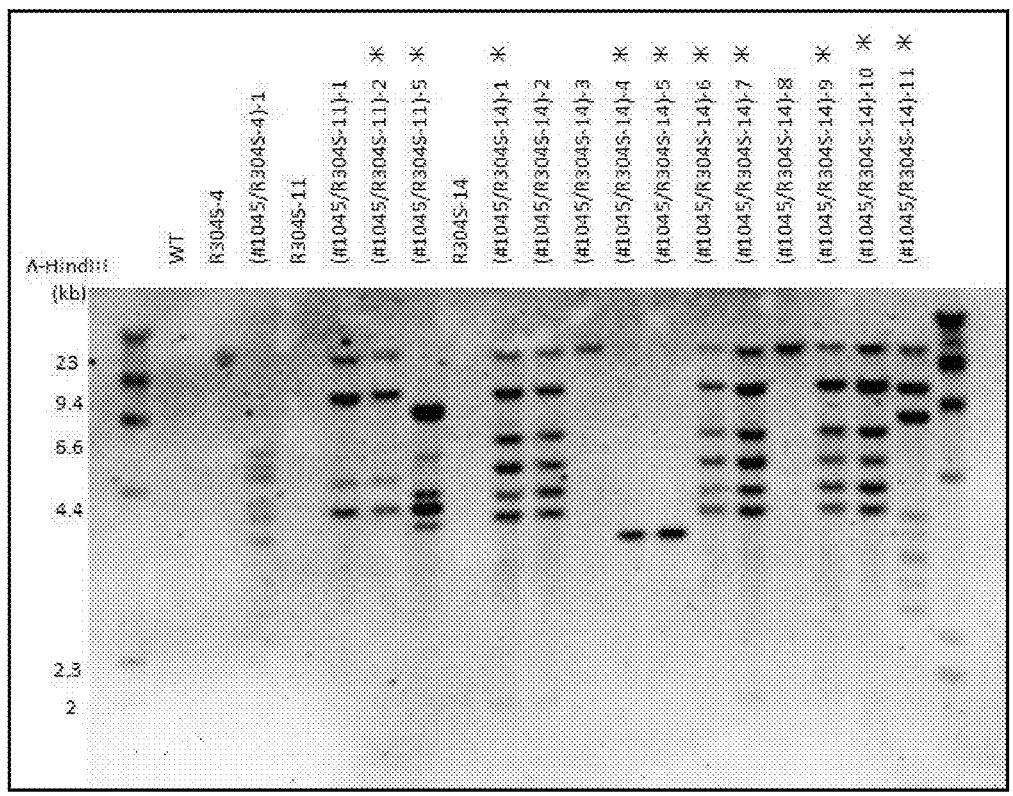
FIG. 12 is a photograph of a membrane for illustrating the result of the Southern blotting analysis shown in FIG. 11. Note that, in the figure, re-differentiated plants exhibiting the same band pattern are presumably derived from the same cell.

Moreover, the membrane shown in FIG. 10 was stripped, and Southern blotting was performed using an HPT gene to be positioned on #1045 as a probe (see FIG. 11). The result confirmed the insertion of I-SceI into the genome as shown in FIG. 12.

Thus, from the GT calli of the 95 individuals, nine transformed rice individuals (9.5%) were obtained from which the positive selectable marker was removed.

Reference Example 1

NPL 2 states that a T-DNA having a reporter gene in which a marker gene and recognition sites of a nuclease I-SceI disposed on both ends of the marker gene are inserted is introduced into plant cells, and that the marker gene can be removed from the reporter gene by expressing I-SceI in a plant cell in which the reporter gene is randomly inserted in the genomic DNA. Further, it is stated that, by matching (overlapping) 600-bp sequences located outside the recognition sites in the T-DNA, after the marker gene is excised, homologous recombination occurs between the overlapping DNA sequences of broken ends, and the I-SceI recognition sites are also successfully removed.

However, in the method described in NPL 2, homologous recombination occurs between the overlapping DNA sequences before I-SceI is expressed. As a result, the marker gene is removed in quite a large amount from the genomic DNAs. This makes it difficult to select a plant cell, in which a reporter gene is randomly inserted in the genomic DNA, based on an expression of the marker gene.

On the other hand, the present invention with the short overlapping DNA sequences of at least 30 nucleotides as described above makes it possible, in the method for introducing a mutation into a target DNA on the genome of a plant cell via homologous recombination, to stably select a plant cell, in which the mutation is introduced, based on an expression of a marker gene. Further, the present invention also makes it possible to remove an unnecessary sequence such as the marker gene in the selected cell, and to introduce only a required mutation into the target DNA.

Figure 13:
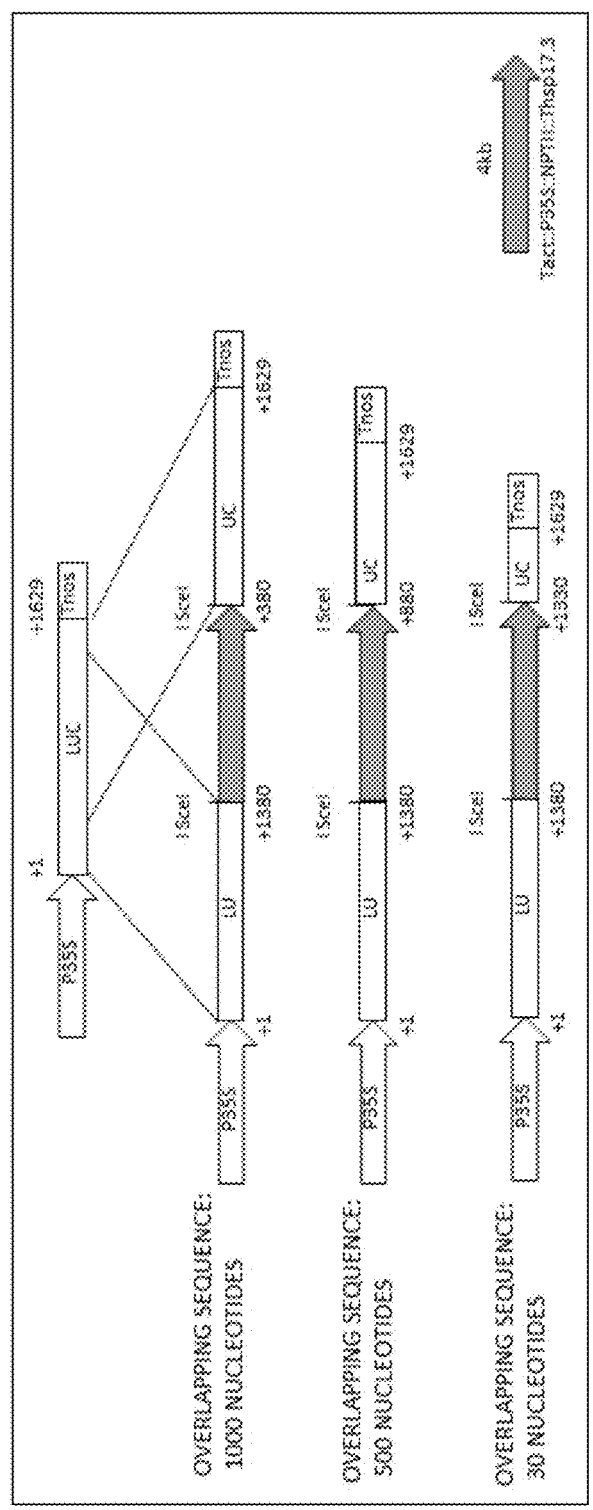
FIG. 13 is a schematic diagram showing reporter systems for evaluating the correlation of the number of nucleotides in short overlapping DNA sequences with the frequency of homologous recombination between the short overlapping DNA sequences in the absence of nuclease expression.

Hence, the correlation of the number of nucleotides in short overlapping DNA sequences with the frequency of homologous recombination between the short overlapping DNA sequences in the absence of nuclease expression was evaluated by constructing reporter systems shown in FIG. 13.

To be more specific, first, T-DNAs shown in FIG. 13 were constructed. Each of the T-DNAs had a reporter gene (luciferase gene) in which a marker gene (NPTII gene) and recognition sites of I-SceI disposed on both ends of the marker gene were inserted.

Note that, in the T-DNA, the sequences of 1000 nucleotides, 500 nucleotides, or 30 nucleotides located outside the recognition sites are matched (overlapped) with each other. Hence, when homologous recombination occurs between these overlapping sequences in a rice callus comprising this T-DNA introduced, the marker gene and the recognition sites are removed from the reporter gene. Then, the reporter gene is re-constructed, making it possible to express a luciferase protein to be encoded. For this reason, based on chemiluminescence produced when the substrate luciferin is degraded, the presence or absence of the homologous recombination can be analyzed.

Figure 14:
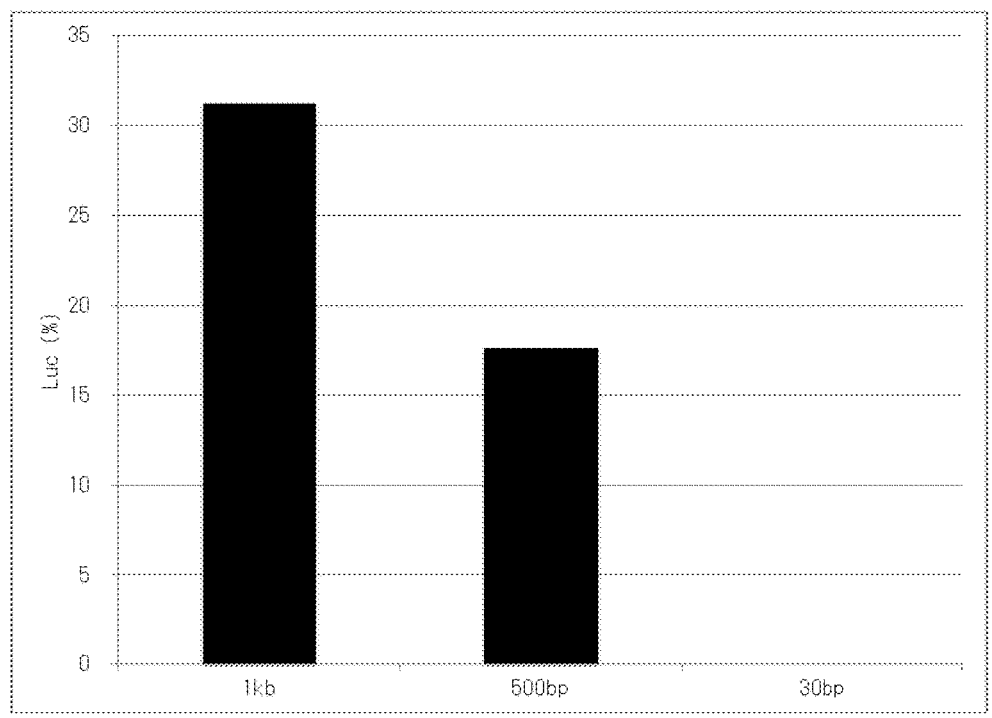
FIG. 14 is a graph showing the analysis result obtained by using the reporter systems shown in FIG. 13. In the figure, the horizontal axis represents the number of nucleotides in the short overlapping DNA sequences in the reporter systems shown in FIG. 13, while the vertical axis represents a ratio between calli from which the reporter expression was detected and calli in which the reporter systems shown in FIG. 13 were introduced.

The three types of T-DNAs having the overlapping sequences different in length were each introduced into rice calli by the same method as in Examples described above. Two months later, chemiluminescences by luciferase in these calli were detected. FIG. 14 shows the obtained result.

As shown in FIG. 14, in the system where the length of the overlapping sequences was 1000 nucleotides, the luminescence by luciferase was detected, even partially in some cases, in eight calli out of 24 calli without expressing I-SceI. It was verified that homologous recombination occurred between the overlapping sequences in approximately 30% of the calli. On the other hand, it was revealed that, with the overlapping sequences of 500 nucleotides, the frequency was lowered down to approximately 15%; further, with 30 nucleotides, the occurrence of the homologous recombination was completely suppressed in the absence of I-SceI expression.

INDUSTRIAL APPLICABILITY

In GT targeting a gene into which a mutation is to be introduced without providing a selected trait by the mutation itself, it is necessary to utilize an exogenous selectable marker. Moreover, in a case where a minimum modification is to be added to an endogenous gene so as to consequently introduce a mutation equivalent to a spontaneous mutation, the technology of removing a selectable marker without any trace after the GT is very important.

As described above, the present invention enables, in the method for introducing a mutation into a target DNA on the genome of a plant cell via homologous recombination: stable selection of a plant cell, in which the mutation is introduced, based on an expression of a marker gene; the subsequent removal of an unnecessary sequence such as the marker gene from the selected cell; and the introduction of only a required mutation into the target DNA.

Therefore, the method for producing a plant cell comprising a mutation introduced in a target DNA and so forth of the present invention are useful in the fundamental research such as gene function analysis. Moreover, useful crop plants produced by minimum gene modification are conceivably more acceptable to society than conventional genetically modified crops. Accordingly, the present invention is very useful in the development of breeding materials.

SEQUENCE LISTING FREE TEXT

SEQ ID NOs: 1 to 7 and 11 to 21
<223> Artificially synthesized primer sequence
SEQ ID NO: 8
<223> PDS 7311-7340
SEQ ID NO: 9
<223> I-SceI Forward
SEQ ID NO: 10
<223> I-SceI Reverse

The invention claimed is:

1. A method for producing a plant cell comprising a mutation introduced in a target DNA, the method comprising the following steps (i) to (iii):
   (i) a step of introducing into plant cells a DNA construct comprising a marker gene, and a first DNA and a second DNA homologous to a target DNA, the DNA construct having the following features (a) to (d):
      (a) the first homologous DNA is located at the 5' side of the marker gene, and a nuclease recognition site is present between said first homologous DNA and said marker gene,
      (b) the second homologous DNA is located at the 3' side of the marker gene, and a nuclease recognition site is present between said second homologous DNA and said marker gene,
      (c) the 3' end region of the first homologous DNA and the 5' end region of the second homologous DNA are DNA sequences that contain between 30 to 100 nucleotides homologous to each other, and
      (d) in at least one of said first homologous DNA and said second homologous DNA, a desired mutation is introduced in a region other than in said DNA sequences that contain between 30 to 100 nucleotides homologous to each other,
   (ii) a step of selecting a plant cell, in which the mutation and the marker gene flanked by said nuclease recognition sites are introduced in the target DNA via homologous recombination between the target DNA and the first and second homologous DNAs, based on expression of the marker gene; and (iii) a step of removing the marker gene and said nuclease recognition sites from the target DNA by expressing a nuclease, or nucleases, capable of specifically recognizing said nuclease recognition sites in the cell selected in the step (ii).

2. The method according to claim 1, wherein at least one nuclease is I-SceI.

3. A plant cell comprising a marker gene flanked by nuclease recognition sites, and the following mutation introduced in a target DNA via homologous recombination with a first DNA and a second DNA homologous to the target DNA, by introducing a DNA construct comprising the marker gene and the first and second homologous DNAs, the DNA construct having the following features (a) to (d):
   (a) the first homologous DNA is located at the 5' side of the marker gene, and a nuclease recognition site is present between said first homologous DNA and said marker gene;
   (b) the second homologous DNA is located at the 3' side of the marker gene, and a nuclease recognition site is present between said second homologous DNA and said marker gene;
   (c) the 3' end region of the first homologous DNA and the 5' end region of the second homologous DNA are DNA sequences that contain between 30 to 100 nucleotides homologous to each other; and
   (d) in at least one of said first homologous DNA and said second homologous DNA, a desired mutation is introduced in a region other than in said DNA sequences that contain between 30 to 100 nucleotides homologous to each other.

4. The plant cell according to claim 3, wherein at least one of the nuclease recognition sites is recognized by I-SceI.

5. A DNA construct comprising: a marker gene; and a first DNA and a second DNA homologous to a target DNA, the DNA construct having the following features (a) to (d):
   (a) the first homologous DNA is located at the 5' side of the marker gene, and a nuclease recognition site is present between said first homologous DNA and said marker gene:
   (b) the second homologous DNA is located at the 3' side of the marker gene, and a nuclease recognition site is present between said second homologous DNA and said marker gene;
   (c) the 3' end region of the first homologous DNA and the 5' end region of the second homologous DNA are DNA sequences that contain between 30 to 100 nucleotides homologous to each other; and
   (d) in at least one of said first homologous DNA and said second homologous DNA, a desired mutation is introduced in a region other than in said DNA sequences that contain between 30 to 100 nucleotides homologous to each other.

6. A kit for use in the method according to claim 1, the kit comprising the following (A) and (B):
   (A) a DNA construct comprising: a marker gene; and a first DNA and a second DNA homologous to a target DNA, the DNA construct having the following features (a) to (d):
      (a) the first homologous DNA is located at the 5' side of the marker gene, and a nuclease recognition site is present between said first homologous DNA and said marker gene;
      (b) the second homologous DNA is located at the 3' side of the marker gene, and a nuclease recognition site is present between said second homologous DNA and said marker gene;
      (c) the 3' end region of the first homologous DNA and the 5' end region of the second homologous DNA are DNA sequences that contain between 30 to 100 nucleotides homologous to each other; and
      (d) in at least one of said first homologous DNA and said second homologous DNA, a desired mutation is introduced in a region other than in said DNA sequences that contain between 30 to 100 nucleotides to each other; and
   (B) a DNA construct for expressing in a plant cell a nuclease, or nucleases, capable of specifically recognizing said nuclease recognition sites.

7. The method according to claim 1, wherein upon cleavage, said nuclease recognition sites do not leave nucleotide overhangs complementary to each other.

8. The method according to claim 2, wherein upon cleavage, said nuclease recognition sites do not leave nucleotide overhangs complementary to each other.

9. The method according to claim 3, wherein said nuclease recognition sites, when cleaved, do not leave nucleotide overhangs complementary to each other.

10. The method according to claim 4, wherein said nuclease recognition sites, when cleaved, do not leave nucleotide overhangs complementary to each other.

11. The method according to claim 5, wherein said nuclease recognition sites, when cleaved, do not leave nucleotide overhangs complementary to each other.

12. The method according to claim 6, wherein said nuclease recognition sites, when cleaved, do not leave nucleotide overhangs complementary to each other.

* * * * *

SEQUENCE LISTING

<160> NUMBER OF SEQ ID NOS: 25

<210> SEQ ID NO 1

```
<211> LENGTH: 37
<212> TYPE: DNA
<213> ORGANISM: Artificial Sequence
<220> FEATURE:
<223> OTHER INFORMATION: Artificially synthesized primer sequence

<400> SEQUENCE: 1
ttctggcgcg cctgcatgag gaggcaaacg aggtcct                                37

<210> SEQ ID NO 2
<211> LENGTH: 44
<212> TYPE: DNA
<213> ORGANISM: Artificial Sequence
<220> FEATURE:
<223> OTHER INFORMATION: Artificially synthesized primer sequence

<400> SEQUENCE: 2
accctgttat ccctagctta aacctgtgca aaaggatctg ggca                        44

<210> SEQ ID NO 3
<211> LENGTH: 37
<212> TYPE: DNA
<213> ORGANISM: Artificial Sequence
<220> FEATURE:
<223> OTHER INFORMATION: Artificially synthesized primer sequence

<400> SEQUENCE: 3
ttctggcgcg cctgcatgag gaggcaaacg aggtcct                                37

<210> SEQ ID NO 4
<211> LENGTH: 39
<212> TYPE: DNA
<213> ORGANISM: Artificial Sequence
<220> FEATURE:
<223> OTHER INFORMATION: Artificially synthesized primer sequence

<400> SEQUENCE: 4
gaagttaatt aattaccctg ttatccctag cttaaacct                              39

<210> SEQ ID NO 5
<211> LENGTH: 45
<212> TYPE: DNA
<213> ORGANISM: Artificial Sequence
<220> FEATURE:
<223> OTHER INFORMATION: Artificially synthesized primer sequence

<400> SEQUENCE: 5
accctgttat ccctatgccc agatcctttt gcacaggttt aagct                       45

<210> SEQ ID NO 6
<211> LENGTH: 40
<212> TYPE: DNA
<213> ORGANISM: Artificial Sequence
<220> FEATURE:
<223> OTHER INFORMATION: Artificially synthesized primer sequence

<400> SEQUENCE: 6
attgttaatt aaagtgagtg caaagggaga taaggtctct                             40

<210> SEQ ID NO 7
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 7
```

```
aattggcgcg ccattaccct gttatcccta tgcccagatc ct                 42

<210> SEQ ID NO 8
<211> LENGTH: 30
<212> TYPE: DNA
<213> ORGANISM: Artificial Sequence
<220> FEATURE:
<223> OTHER INFORMATION: PDS 7311-7340

<400> SEQUENCE: 8
tgcccagatc cttttgcaca ggtttaagct                               30

<210> SEQ ID NO 9
<211> LENGTH: 18
<212> TYPE: DNA
<213> ORGANISM: Artificial Sequence
<220> FEATURE:
<223> OTHER INFORMATION: I-SceI Forward

<400> SEQUENCE: 9
tagggataac agggtaat                                            18

<210> SEQ ID NO 10
<211> LENGTH: 18
<212> TYPE: DNA
<213> ORGANISM: Artificial Sequence
<220> FEATURE:
<223> OTHER INFORMATION: I-SceI Reverse

<400> SEQUENCE: 10
atccctattg tcccatta                                            18

<210> SEQ ID NO 11
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 11
acatacccat ccaacaatgt tcaatccctt                               30

<210> SEQ ID NO 12
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 12
tggatttgta gagttagaaa tacctgactt                               30

<210> SEQ ID NO 13
<211> LENGTH: 26
<212> TYPE: DNA
<213> ORGANISM: Artificial Sequence
<220> FEATURE:
<223> OTHER INFORMATION: Artificially synthesized primer sequence

<400> SEQUENCE: 13
tgatggactg attggctgat ggtggt                                   26

<210> SEQ ID NO 14
<211> LENGTH: 30
<212> TYPE: DNA
```

```
<213> ORGANISM: Artificial Sequence
<220> FEATURE:
<223> OTHER INFORMATION: Artificially synthesized primer sequence

<400> SEQUENCE: 14
ctgacgatga gaatatatct gatgctgtga                                    30

<210> SEQ ID NO 15
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 15
ttgaacaaga tggattgcac                                                20

<210> SEQ ID NO 16
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 16
ggcatcgcca tgtgtcacga                                                20

<210> SEQ ID NO 17
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 17
aggtagaaat gccatgcggg aagt                                           24

<210> SEQ ID NO 18
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 18
tccgacttgg aaccaaataa ttca                                           24

<210> SEQ ID NO 19
<211> LENGTH: 23
<212> TYPE: DNA
<213> ORGANISM: Artificial Sequence
<220> FEATURE:
<223> OTHER INFORMATION: Artificially synthesized primer sequence

<400> SEQUENCE: 19
tcacattggg aagaactggc agt                                            23

<210> SEQ ID NO 20
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 20
tgcaaggtac taactaggag acatt                                          25
```

```
<210> SEQ ID NO 21
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 21
ttgtaaacag atctgtaaca gtga                                          24

<210> SEQ ID NO 22
<211> LENGTH: 58
<212> TYPE: DNA
<213> ORGANISM: Artificial Sequence
<220> FEATURE:
<223> OTHER INFORMATION: sequence with PDS 7311-7340

<400> SEQUENCE: 22
tgcccagatc cttttgcaca ggtttaagct agggataaca gggtaattaa ttaacttc     58

<210> SEQ ID NO 23
<211> LENGTH: 58
<212> TYPE: DNA
<213> ORGANISM: Artificial Sequence
<220> FEATURE:
<223> OTHER INFORMATION: complementary sequence

<400> SEQUENCE: 23
gaagttaatt aattaccctg ttatccct agcttaaacc tgtgcaaaag gatctgggca     58

<210> SEQ ID NO 24
<211> LENGTH: 60
<212> TYPE: DNA
<213> ORGANISM: Artificial Sequence
<220> FEATURE:
<223> OTHER INFORMATION: sequence with I-SceI Forward

<400> SEQUENCE: 24
aattggcgcg ccattaccct gttatccct tgcccagatc cttttgcaca ggtttaagct    60

<210> SEQ ID NO 25
<211> LENGTH: 60
<212> TYPE: DNA
<213> ORGANISM: Artificial Sequence
<220> FEATURE:
<223> OTHER INFORMATION: complementary sequence

<400> SEQUENCE: 25
agcttaaacc tgtgcaaaag gatctgggca tagggataac agggtaatgg cgcgccaatt   60
```